US012709766B2

(12) United States Patent
Gavara et al.

(10) Patent No.: US 12,709,766 B2
(45) Date of Patent: Aug. 18, 2026

(54) METHOD FOR PREPARATION OF GLYCOLIPID CARBOXYLIC ACIDS

(71) Applicant: ANTHEM BIOSCIENCES PRIVATE LIMITED, Bangalore (IN)

(72) Inventors: Govinda Rajulu Gavara, Bangalore (IN); Sumesh Eswaran, Bangalore (IN); Rajendra Gaikwad, Bangalore (IN); Amresh Kumar, Bangalore (IN); Ganesh Sambasivam, Bangalore (IN)

(73) Assignee: Anthem Biosciences Private Limited, Bangalore (IN)

( * ) Notice: Subject to any disclaimer, the term of this patent is extended or adjusted under 35 U.S.C. 154(b) by 199 days.

(21) Appl. No.: 18/574,060

(22) PCT Filed: Jun. 24, 2022

(86) PCT No.: PCT/IB2022/055884
§ 371 (c)(1),
(2) Date: Dec. 25, 2023

(87) PCT Pub. No.: WO2022/269561
PCT Pub. Date: Dec. 29, 2022

(65) Prior Publication Data

US 2024/0318217 A1 Sep. 26, 2024

(30) Foreign Application Priority Data

Jun. 25, 2021 (IN) ............................ 202141028550

(51) Int. Cl.
*C12P 19/26* (2006.01)
*C07H 15/08* (2006.01)
*C12N 9/20* (2006.01)

(52) U.S. Cl.
CPC .............. *C12P 19/26* (2013.01); *C07H 15/08* (2013.01); *C12N 9/20* (2013.01); *C12Y 301/01003* (2013.01)

(58) Field of Classification Search
CPC ........................................................ C12P 7/40
See application file for complete search history.

(56) References Cited

U.S. PATENT DOCUMENTS

| | | | | |
|---|---|---|---|---|
| 5,208,156 | A | 5/1993 | Shibatani et al. | |
| 5,773,266 | A | 6/1998 | Bosley et al. | |
| 2019/0206904 | A1 | 7/2019 | Zhou et al. | |
| 2019/0209604 | A1* | 7/2019 | Zhang | C12N 15/117 |

FOREIGN PATENT DOCUMENTS

| | | | | |
|---|---|---|---|---|
| EP | 1319714 B1 * | 6/2005 | | C12P 7/40 |
| WO | WO-2014025805 A1 * | 2/2014 | | C07H 1/00 |

OTHER PUBLICATIONS

Sugai et al., "Chemo-Enzymatic Synthesis of (R,R)-(−)-Pyrenophorin" Tetrahedron vol. 51 No. 44 pp. 11987-11998 (Year: 1995).*
English machine translation of EP1319714, downloaded from worldwide.espacenet.com (Year: 2003).*
International Search Report dated Dec. 6, 2022, Application No. PCT/IB22/55884.

* cited by examiner

*Primary Examiner* — Andrea Olson
(74) *Attorney, Agent, or Firm* — The Dobrusin Law Firm, P.C.

(57) ABSTRACT

The present invention relates to a method of preparation of Glycolipid carboxylic acids of Formula I by selective hydrolysis of corresponding esters by enzymes. The method provides preparation of compounds of Formula I in high yield by an environmentally benign, robust, economical, simple and convenient method.

Formula I

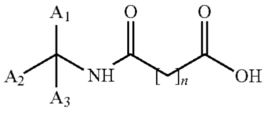

11 Claims, No Drawings

METHOD FOR PREPARATION OF GLYCOLIPID CARBOXYLIC ACIDS

CROSS REFERENCE TO RELATED APPLICATION

The present application claims priority to Indian provisional patent application No. 202141028550, filed on Jun. 25, 2021. The entire content of the aforementioned application is specifically incorporated herein by reference.

TECHNICAL FIELD

The present disclosure is in relation to synthetic organic chemistry. The invention is in relation to a method of preparation of Glycolipid carboxylic acids and its derivatives. The method involves selective hydrolysis of Glycolipid carboxylic esters using enzymes. In particular, the method involves preparation of compounds of Formula I by selective hydrolysis of Glycolipid carboxylic esters to corresponding carboxylic acids using enzymes. The method provides an economical and environmentally benign approach to prepare complex organic compounds in high yield.

BACKGROUND OF THE INVENTION

Glycolipids are essential constituents of cellular membranes consisting of a sugar and lipid moiety. It is ubiquitously known that Glycolipids are important for cell aggregation, dissociation and also in specific cellular contact and for signal transduction. It also acts as a promising delivery system in RNA interference (RNAi) therapeutics. This application is broadly used as a potential therapeutic to reversibly silence any gene and has gained impetus in research. To achieve the clinical potential of RNAi, delivery materials are required to transport short interfering RNA (siRNA) to the site of action in the cells of target tissues.

Glycolipids such as N-Acetylgalactosamine (GalNAc) and its derivatives are prominent material amongst the said compounds for delivery of drugs. Its conjugates have been developed by directly conjugating delivery material to the siRNA cargo. This approach leads to well-defined, single-component system that uses only equimolar amounts of delivery material and siRNA. Therapeutics demand compounds in pristine form to minimize undesirable side effect, dosage. However, getting pristine compound is a challenge, specifically with the said complex molecules.

N-Acetylgalactosamine (GalNAc) or its derivatives are sensitive Glycolipids due to large structure and easily susceptible functional groups.

Migawa, Michael T., et al. "A convenient synthesis of 5'-triantennary N-acetyl-galactosamine clusters based on nitromethanetrispropionic acid." *Bioorganic & Medicinal Chemistry Letters* 26.9 (2016): 2194-2197 reports a method for the synthesis of several triantennary GalNAc clusters based on a nitromethanetrispropionic acid core was developed. The synthetic approach involves pentafluorophenolic ester intermediates which can be used in a one-pot, seven reaction procedure to prepare a variety of triantennary GalNAc conjugated ASOs.

WO 2014/025805A1 reports the production of triantennary GalNAc derivatives.

However, the prior art methods to prepare said compounds involve harsh reaction conditions, multiple steps, low yields of the target compound. The conventional methods of preparation are difficult for large-scale production and also uneconomical.

Considering the significance of the glycolipid compounds, it is necessary to develop a robust, economical and environmentally benign method to prepare said complex glycolipids and its potential intermediates. The present inventors have surprisingly developed an efficient method for the preparation of Glycolipid carboxylic acids and its derivatives which fulfills the aforesaid requirements and ameliorates the shortcomings of the prior art.

OBJECTS OF THE INVENTION

It is an object of the present invention to provide an efficient method for the preparation of Glycolipid carboxylic acids and its derivatives.

It is another object of the present invention to provide an efficient method which is robust, economical, simple, involves lesser steps and environmentally benign.

It is another object of the present invention to provide an efficient method which provides Glycolipid carboxylic acids and its derivatives at high yield and purity.

It is yet another object of the present invention to provide a method for the preparation of compounds of Formula I.

SUMMARY OF THE INVENTION

According to an aspect of the present invention there is provided a method for preparation of glycolipid carboxylic acids and its derivatives. The glycolipid carboxylic acids and derivatives prepared are N-Acetylgalactosamine (GalNAc) derivatives.

According to another aspect of the present invention there is provided a method of preparation of compounds of Formula I and its intermediates involving selective hydrolysis using enzymes. The compounds of Formula I can be adopted as key intermediates in the preparation of therapeutically important Glycolipids.

According to an aspect of the present invention there is provided a process for preparing compounds of Formula (I):

Formula I

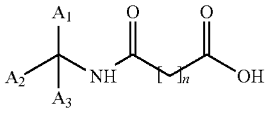

According to another aspect of the present invention there is provided a process for preparing compounds of Formula (I'):

Formula (I')

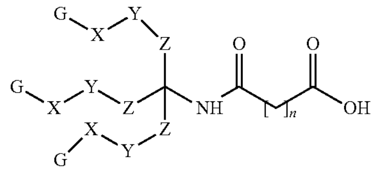

According to yet another aspect of the present invention there is provided a process for preparing a compound of Formula (1-e):

1-e

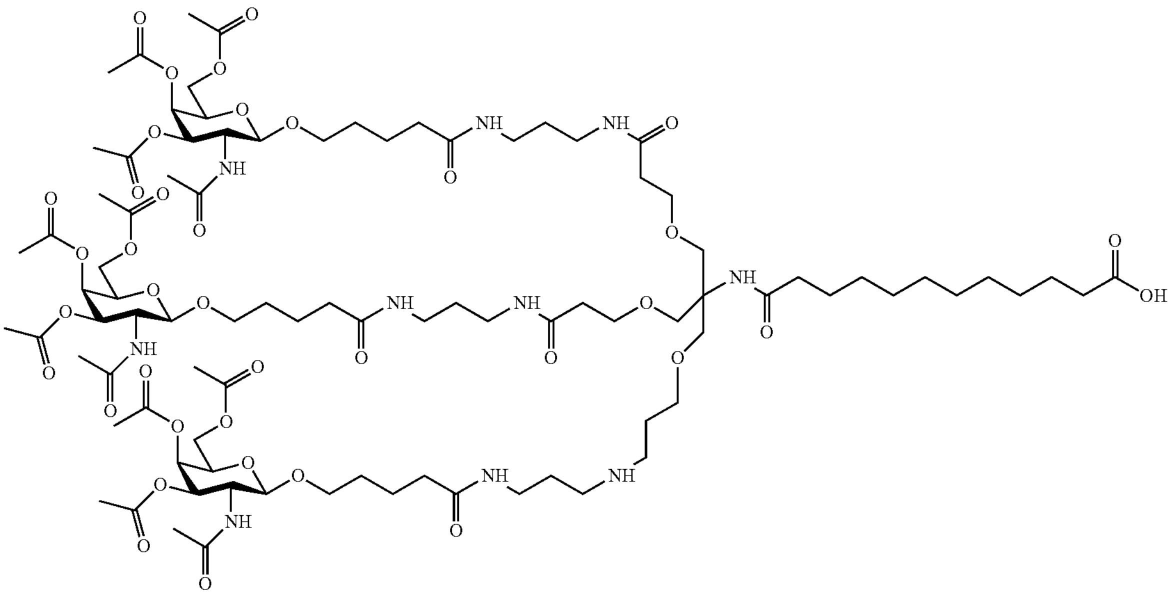

According to yet another aspect of the present invention there is provided Compounds of Formula (I) and Formula (I').

DETAILED DESCRIPTION OF THE INVENTION

The following description with reference to the accompanying drawings is provided to assist in a comprehensive understanding of exemplary embodiments of the invention. It includes various specific details to assist in that understanding but these are to be regarded as merely exemplary.

Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the scope of the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, steps or components but does not preclude the presence or addition of one or more other features, steps, components or groups thereof.

The present invention relates to a method of selective hydrolysis of Glycolipid carboxylic acid esters using enzymes. In particular, the method involves preparation of Glycolipid carboxylic acids and its derivatives of Formula I by selective hydrolysis of corresponding Glycolipid carboxylic esters using enzymes. The method provides an economical and environmentally benign approach to prepare complex organic compounds in high yield.

The present invention provides enzymatic hydrolysis of ester to acids and efficient way of making compounds of Formula I via enzymatic process.

Scheme A
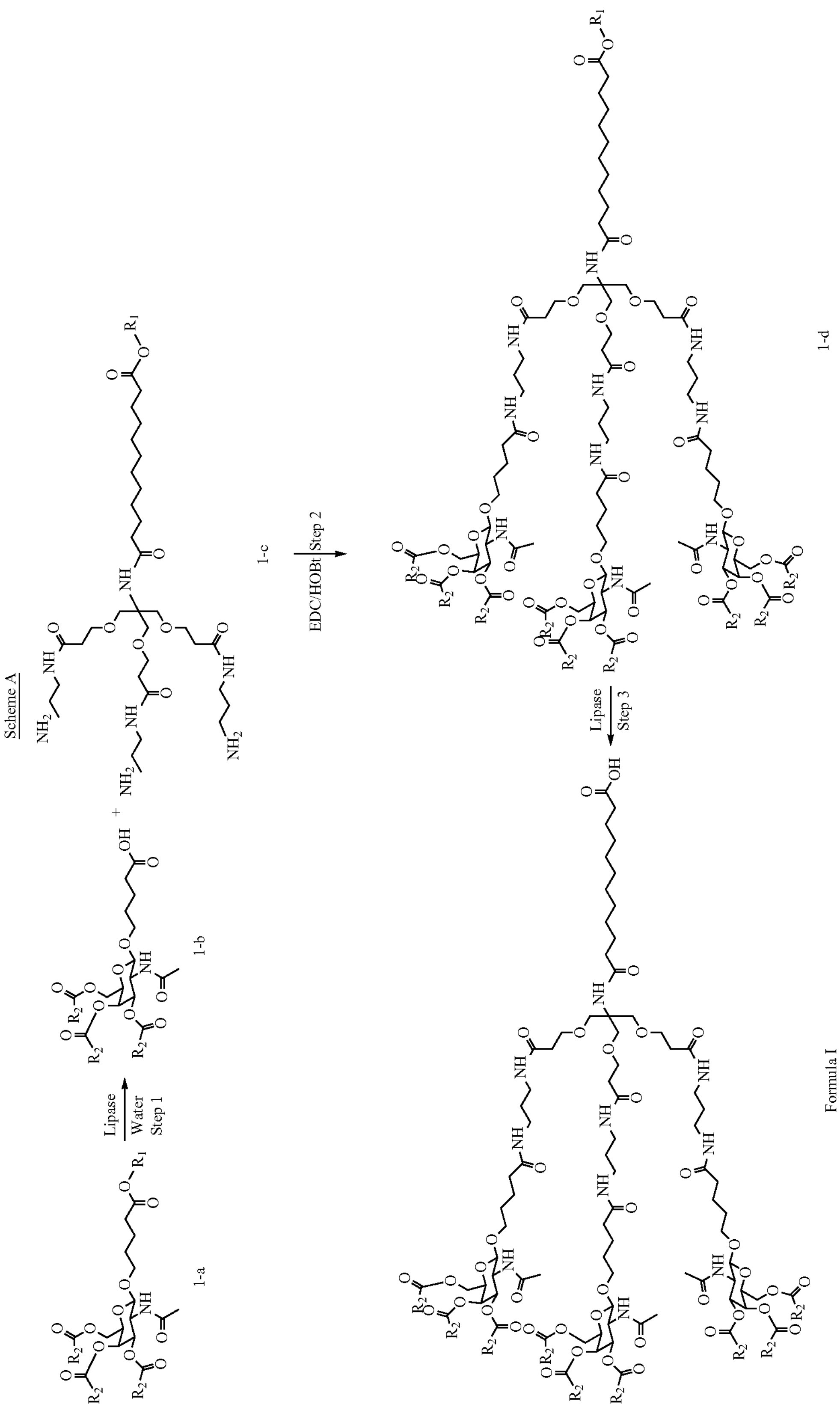
1-a
1-b
1-c
1-d
Formula I

The present invention provides a process for preparing compounds of Formula (I)

Formula I

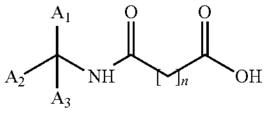

Wherein:

"n" ranges from 1-15;

$A_1$, $A_2$ and $A_3$ are each independently selected from H or

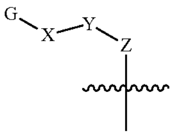

Provided that $A_1$. $A_2$ and $A_3$ together are not H;

G is selected from the following groups:

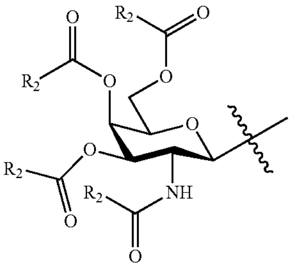

or

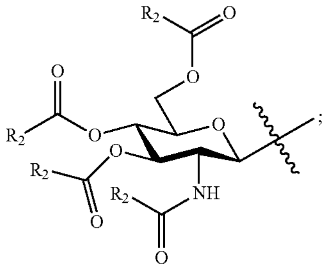

;

X is selected from the following groups:

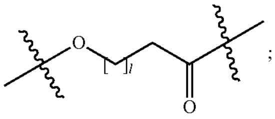

;

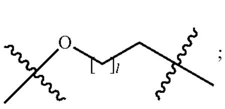

;

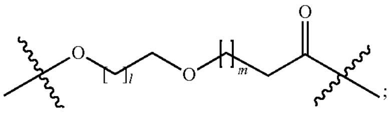

;

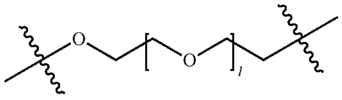

or

-continued

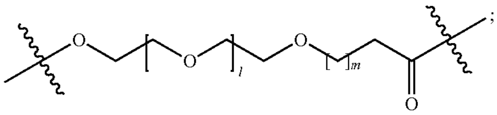

;

Y is selected from

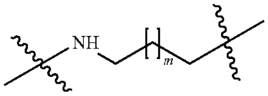

;

and

Z is selected from the following groups:

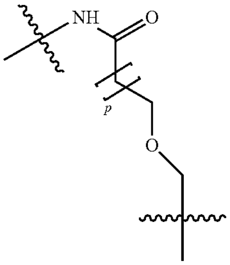

or

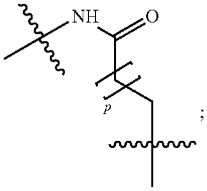

;

Wherein $R_2$ is selected from alkyl, aryl, alkoxy, aryloxy or arylalkyl groups;

"l", "m" and "p" each independently ranges from 0-15;

Comprising the step of:

(a) Subjecting the compound of Formula (Ia)

Formula Ia

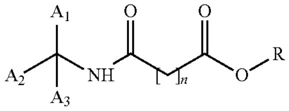

wherein R is selected from alkyl, aryl or aralkyl groups to hydrolysis in the presence of enzyme and water;

(b). Stirring the reaction mixture of step (a) followed by concentrating, drying and dilution with solvent;

(c). Removal of the enzyme solid precipitate from the reaction mixture of step (b) followed by purification to obtain compounds of Formula (I).

In an embodiment, $A_1$, $A_2$ and $A_3$ is each independently

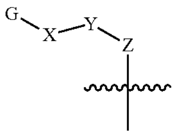

and the substituent
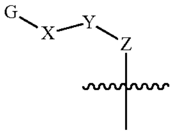
is selected from the following groups:
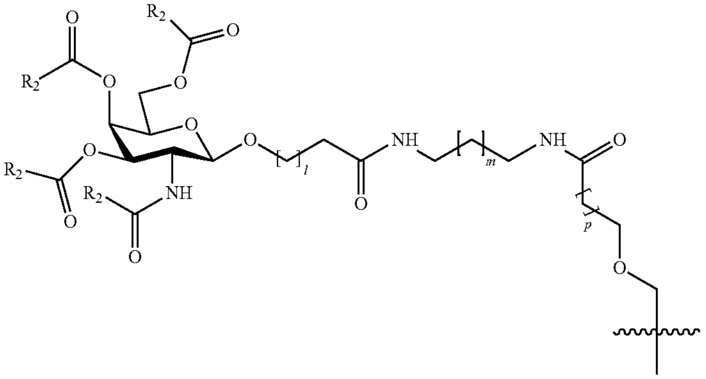
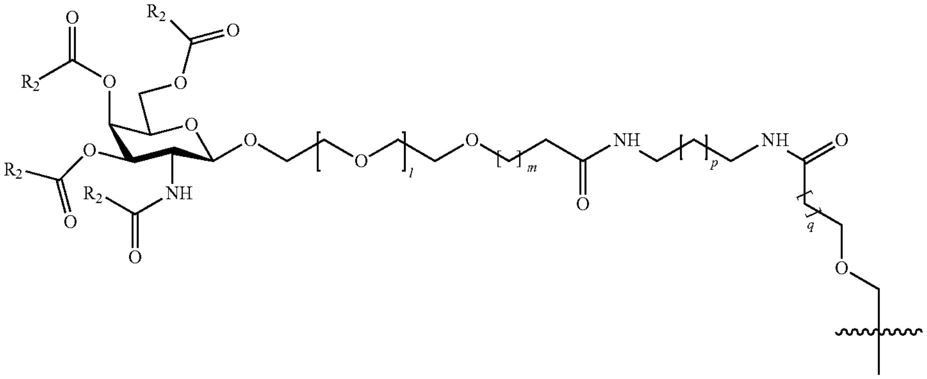
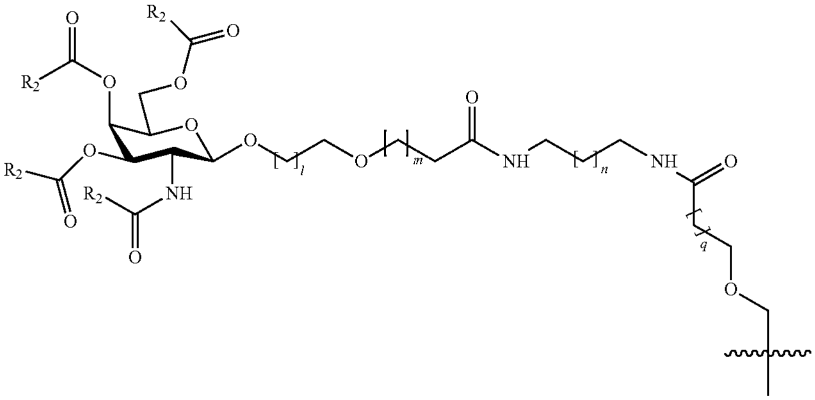

-continued

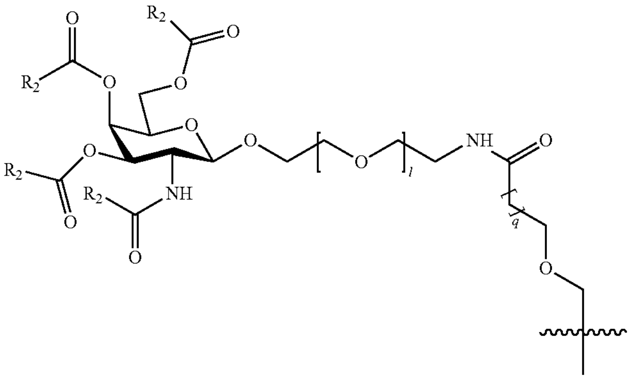

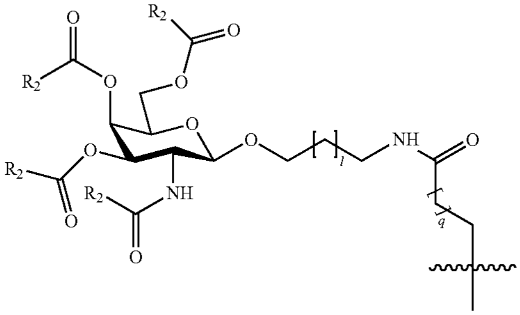

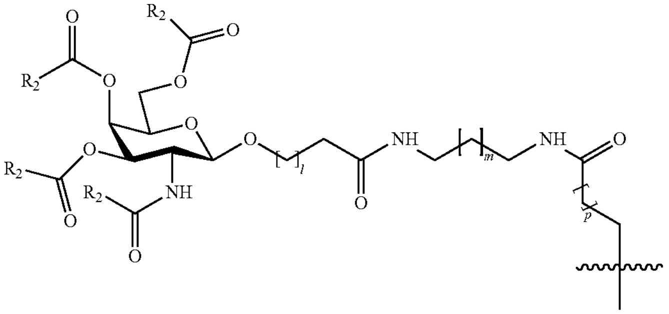

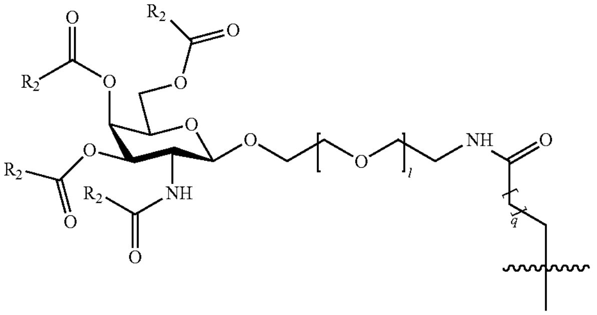

Wherein $R_2$ is selected from alkyl, aryl, alkoxy, aryloxy or arylalkyl groups;

"l", "m", "n" and "p" and "q" each independently ranges from 0-15.

In an embodiment, the enzymes at step (a) are selected from lipases, protease, amylase, trypsin, papain or combinations thereof. In an embodiment, the enzyme is lipase.

In an embodiment, the enzyme at step (a) is present in an amount ranging from 1 to 100% by weight.

In an embodiment, the enzymatic hydrolysis at step (a) is carried out for 1-48 hrs at 20-45° C.

In an embodiment, the solvent at step (b) is selected from water, methanol, ethanol isopropyl alcohol Methyl tert-butyl ether, dichloromethane, ethyl acetate, acetone, dimethyl formamide, tetrahydrofuran and acetonitrile or combinations thereof.

In an embodiment, said groups may be linear, branched, cyclic with or without being substituted with functional groups-selected from but not limiting to halogens, nitro, amine, aldehyde, carbonyl, hydroxyl, and the like.

In an embodiment, the alkyl groups are methyl, ethyl, propyl, isopropyl, butyl, tert-butyl and the like.

In an embodiment, the aryl groups are phenyl, naphthyl groups and the like.

In an embodiment, the aralkyl or substituted aralkyl are Benzyl, p-Methoxy benzyl and the like.

Preferably, the present invention provides a process for preparing compounds of Formula (I') by enzymatic hydrolysis:

Formula (I')

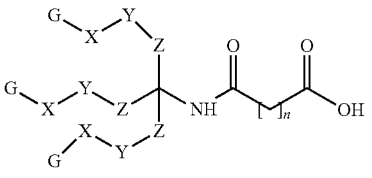

Wherein G, X, Y, Z, $R_2$ are as defined above.

Scheme B

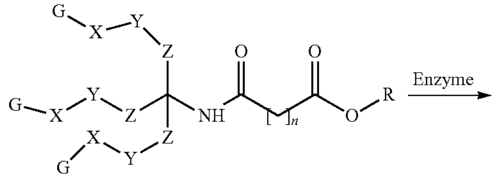

Formula (Ia)'

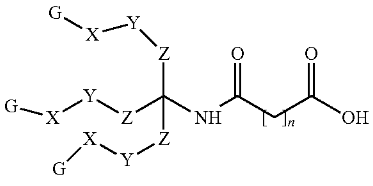

Formula (I)'

The detailed process steps is represented by Scheme C below:

Scheme C

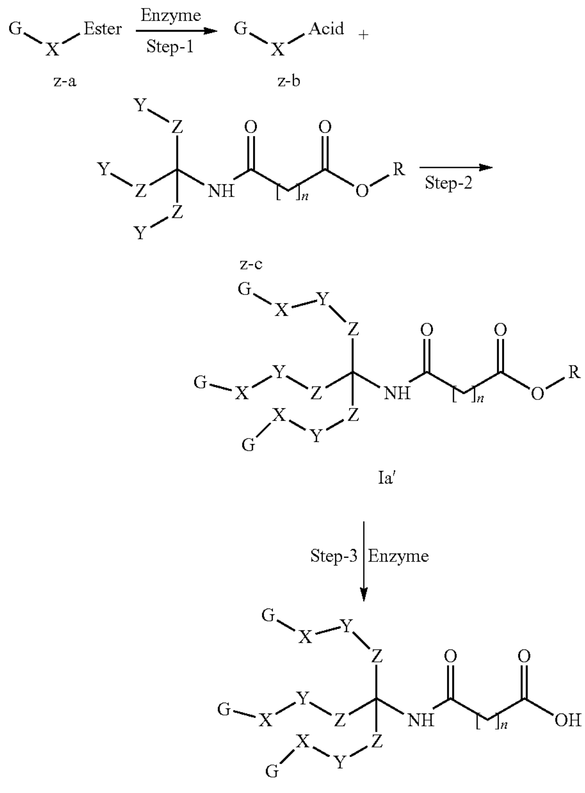

z-a z-b z-c Ia' Formula I'

In another embodiment, the glycolipid amines of formula

Formula (z-bb)

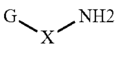

are used as starting reactant instead of Glycolipid carboxylic acids and undergo the same process steps of Step 2 and Step 3 to yield Glycolipid carboxylic acids (compounds of Formula I').

The process comprises the steps of:

(i). Coupling a reactant selected from Glycolipid carboxylic acid of Formula (z-b)

Formula (z-b)

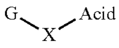

or a Glycolipid amine compound of Formula (z-bb)

Formula (z-bb)

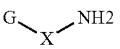

with esters of Formula (z-c)

Formula (z-c)

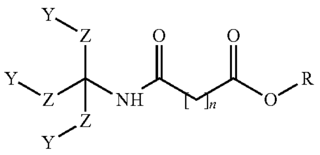

to form compound of Formula (Ia)' and

Formula (Ia)'

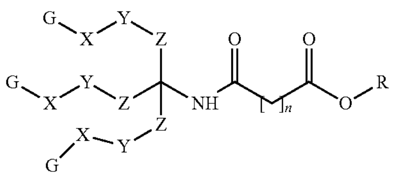

(ii). Subjecting the ester compound of Formula (Ia)' to hydrolysis in presence of enzyme and water to obtain compounds of Formula (I)'.

In an embodiment the reaction parameters like coupling agent, solvent, temperature, pH, reaction time are varied depending upon the enzyme and target compounds of Formula I or its derivatives.

In another embodiment, the pH of the reaction is maintained between 2 and 9; and the reaction temperature can vary between 0° C.-150° C. The reaction time is varied between 2 to 72 hours or till completion of the reaction.

In another embodiment, the solvent for the reaction is selected from protic or aprotic solvents or its combination in appropriate ratio; wherein the protic solvents are water, methanol, ethanol isopropyl alcohol and aprotic solvents are Methyl tert-butyl ether, dichloromethane, ethyl acetate, acetone, dimethyl formamide, tetrahydrofuran and acetonitrile.

In an embodiment, the coupling at step (i) is in presence of a coupling agent selected from a group comprising hydroxybenzotriazole (HOBt), Hexafluorophosphate Benzotriazole Tetramethyl Uronium (HBTU), ethyl-(N',N'-dimethylamino)propylcarbodiimide hydrochloride (EDC·HCL) or combinations thereof.

In an embodiment, the coupling reaction at step (i) is conducted in the presence of a base selected from N,N-diisopropylethylamine (DIPEA).

In an embodiment, the Glycolipid carboxylic acid of Formula (z-b) at step (i) is obtained by;

Subjecting the Glycolipid carboxylic ester of Formula (z-a)

Formula (z-a)

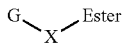

to hydrolysis in presence of enzyme and water to obtain Glycolipid carboxylic acid of Formula (z-b)

EXAMPLES

The following examples are meant to illustrate the present invention. The examples are presented to exemplify the invention and are not to be considered as limiting the scope of the invention.

Example A

Experimental

The detailed process steps are represented by Scheme C:

General Procedure a (Step-1):

To a solution of Glycolipid carboxylic esters (1 eq) in water (5V) was added Enzyme (20% by weight) at 20-25° C. The reaction mixture was allowed to stir for 24-72 hrs at 20-25° C. The completion of the reaction is monitored by TLC. The reaction mixture was concentrated to dryness under reduced pressure at 35° C. The residue obtained was diluted with DCM (15V) and stirred for 20 minutes. The solid precipitate (enzyme) is removed by filtration and filtrate was concentrated under reduced pressure at 35° C. to obtain Glycolipid carboxylic acids.

General Procedure B (Step-2):

To a solution of Glycolipid carboxylic acids (4.5 eq) in DCM (10V) are added HOBt (0.1 eq), DIPEA (10 eq) and EDC·HCl (4.5 eq) at 0-5° C. The reaction mixture was stirred for 10-15 minutes at same temperature and then was added amine (1.0 eq) dissolved in DMF:DCM (1:5) drop-wise passion. The resulting reaction mixture was allowed to stir for 16 h at 20-35° C. The reaction mass was concentrated to dryness, slurred with MTBE (10V×3) and decanted. The residue was dissolved in DCM (10V), washed with water (5V×2), organic layer was dried over sodium sulfate, filtered and concentrated under reduced pressure to afford compounds of Formula (Ia)'.

General Procedure C ((Step-3):

To a solution of Glycolipid carboxylic esters (1 eq) in water (5V) was added Enzyme (5% by weight) at 20-25° C. The reaction mixture was allowed to stir for 12-24 hrs at 20-25° C. The completion of the reaction is monitored by TLC. The reaction mixture was concentrated to dryness under reduced pressure at 35° C. The residue obtained was diluted with DCM (15V) and stirred for 20 minutes. The solid precipitate (enzyme) is removed by filtration and filtrate was concentrated under reduced pressure at 35° C. to obtain Glycolipid carboxylic acids (compounds of Formula I').

In another embodiment, the glycolipid amines of formula

Formula (z-bb)

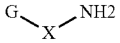

are used as starting reactant instead of Glycolipid carboxylic acids and undergo the same process steps of General procedure B and General procedure C to yield Glycolipid carboxylic acids (compounds of Formula I').

Various commercially available enzymes selected from the list given in Table 1 is adopted for the hydrolysis. In still another embodiment, the enzyme load for the reaction can vary between 1-100% wt/wt. as compared to reactant.

TABLE 1

List of enzymes used for selective hydrolysis according to present invention

| Sr. No | Lipase name | Source (Micro-organism) |
|---|---|---|
| 1 | Lipase CL “Amano” | *Aspergillus oryzae* |
| 2 | Lipase from porcine pancreas | *Porcine pancreas lipase (PPL)* |
| 3 | Lipase AY “Amano”30SD | *Candida cylindracea* |
| 4 | Lipase R “Amano” | *Penicilliumroqueforti* |
| 5 | Lipase A “Amano”12 | *Aspergillus niger* |
| 6 | Lipase MER “Amano” | *Rhizopusoryzae* |
| 7 | Lipase DF “Amano”15 | *Rhizopusoryzae* |
| 8 | Newlase F | *Rhizopusniveus* |
| 9 | Lipase MH “Amano”10SD | *Mucorjavanicus* |
| 10 | Lipase G “Amano”50 Mono, Di-glyceride Lipase | *Penicilliumcamembertii* |
| 11 | Lipase PS “Amano” | *Burkholderiacepacia* |
| 12 | Lipase AK “Amano” | *Burkholderiacepacia* |
| 13 | Lipase PS “Amano” IME | |
| 14 | Novozym 435 (CALB lipase) | *Candida antarctica B* |
| 15 | Lipozyme TL IM | *Thermomyceslanuginosus* |
| 16 | Novozym 40086 | *Rhizomucormehei* |
| 17 | Lipozyme TL 100L | *Thermomyceslanuginosus* |
| 18 | Novocor AD L (CALA) | *Candida antarctica A* |
| 19 | Resinase HT | *Aspergillus oryzae* |
| 20 | Palatase 20000 L | *Rhizomucormiehei* |
| 21 | Novozym 51032 | *Aspergillus micro-organism* |
| 22 | Subtilisin A | *Bacillus subtilis* |
| 23 | Alcalase | |
| 24 | Savinase | |
| 25 | Esperase | |
| 26 | Neutrase | *Bacillus amyloliquefaciens* |
| 27 | rTrypsin | |
| 28 | SPRIN imibond THERMOLYSIN | *Geobacillus* sp. |
| 29 | SPRIN epobond THERMOLYSIN | *Geobacillus* sp. |
| 30 | Protease from *Bacillus Licheniformis* | *Bacillus licheniformis* |
| 31 | Novozym 388 | *Rhizomucormiehei* |
| 32 | Lipex 100L | *Aspergillus oryzae* |
| 33 | Acylase “Amano” | *Aspergillus melleus* |
| 34 | Esperase 8.0 L | *Bacillus lentus* |
| 35 | Lipase AK “Amano” 20 | |
| 36 | Protease N “Amano” | *Bacillus subtilis* |
| 37 | Protease S “Amano” | *Bacillus* sp. |
| 38 | Lipase AS “Amano” | *Aspergillus niger* |
| 39 | Lipase PS “Amano” SD | *Bulkholderiacepacia* |
| 40 | Neutrase 0.8 L | *Bacillus amyloliquefaciens* |
| 41 | Savinase 16L, Type EX | *Bacillus lentus* |
| 42 | ASSEMBLASE liquid | *Escherichia coli* |
| 43 | Lipase AY “Amano” 30SD-K | *Candida rugosa* |
| 44 | Lipase MH “Amano” 10SD | *Mucorjavanicus* |
| 45 | Lipase A “Amano” 12-K | *Aspergillus niger* |
| 46 | Lipase DF “Amano” 15-K | *Rhizopusoryzae* |
| 47 | Papain from papaya latex, P3375-25G | *Carica papaya* |
| 48 | Alcalase | *Bacillus licheniformis* |
| 49 | Trypsin from bovine pancreas cat: 93610 | *Bostaurus* |
| 50 | Lipase PS “Amano” IME | |
| 51 | Lipase IME (90) | |
| 52 | Lipase IME (95) | |
| 53 | Klietase (amylase) | |
| 54 | Amano enzyme CES NL-1 | |
| 55 | Amano enzyme CES NL-2 | |
| 56 | Amano enzyme CES L-1 | |
| 57 | Amano enzyme CES L-2 | |
| 58 | Amano enzyme CES L-3 | |

TABLE 1-continued

List of enzymes used for selective hydrolysis according to present invention

| Sr. No | Lipase name | Source (Micro-organism) |
|---|---|---|
| 59 | Amano enzyme CES L-4 | |
| 60 | Amano enzyme CES L-5 | |

TABLE 1-continued

List of enzymes used for selective hydrolysis according to present invention

| Sr. No | Lipase name | Source (Micro-organism) |
|---|---|---|
| 61 | Amano enzyme CES L-6 | |
| 62 | Amano enzyme CES L-7 | |

Example-1

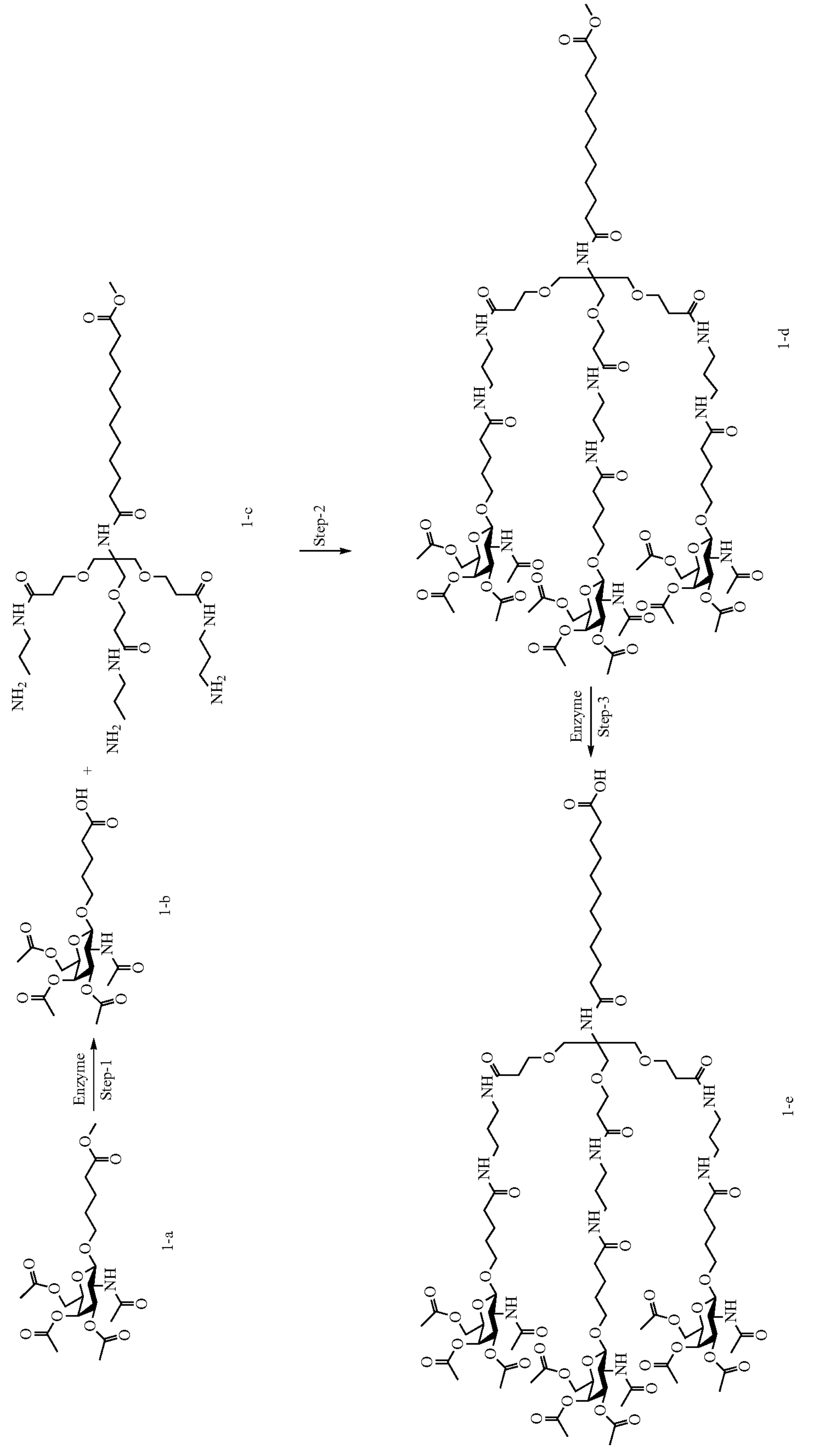
1-a 1-b 1-c 1-d 1-e

Step 1: Preparation of 5-{[4,5-bis(acetyloxy)-6-[(acetyloxy)methyl]-3-acetamidooxan-2-yl]oxy}pentanoic acid (1-b)

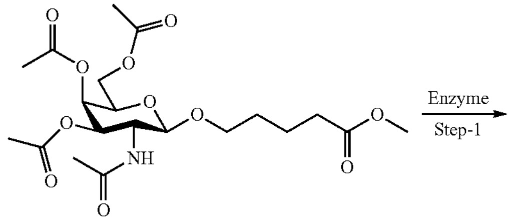

1-a

-continued

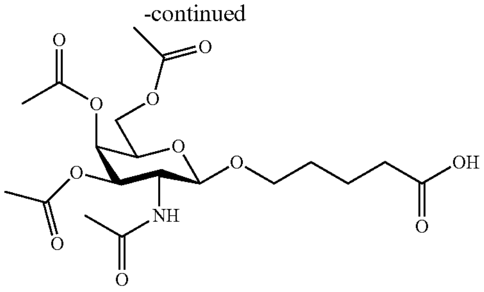

1-b

Compound 1-b was obtained as a white solid (50 g. 89%) according to the General procedure A starting from 1-a.

Step 2: Preparation of methyl 11-{[1,3-bis(2-{[3-(5-{[4,5-bis(acetyloxy)-6-[(acetyloxy)methyl]-3-acetamidooxan-2-yl]oxy}pentanamido)propyl]carbamoyl}ethoxy)-2-[(2-{[3-(5-{[4,5-bis(acetyloxy)-6-[(acetyloxy)methyl]-3-acetamidooxan-2-yl]oxy}pentanamido)propyl]carbamoyl} ethoxy)methyl]propan-2-yl]carbamoyl}undecanoate (1-d)

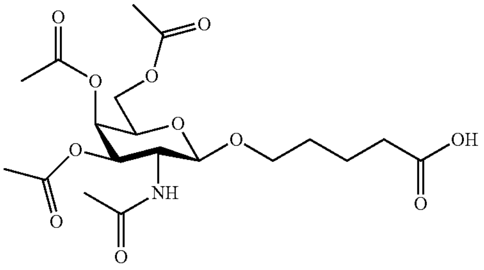

+

1-b

-continued
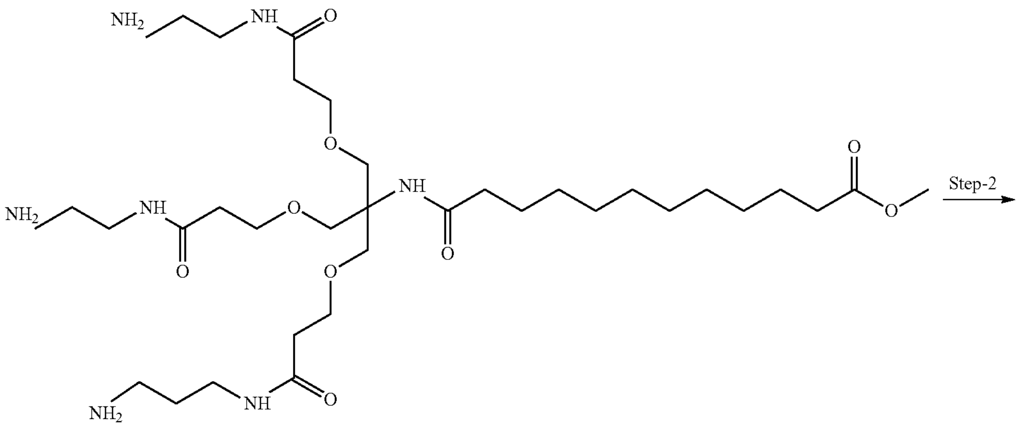
1-c
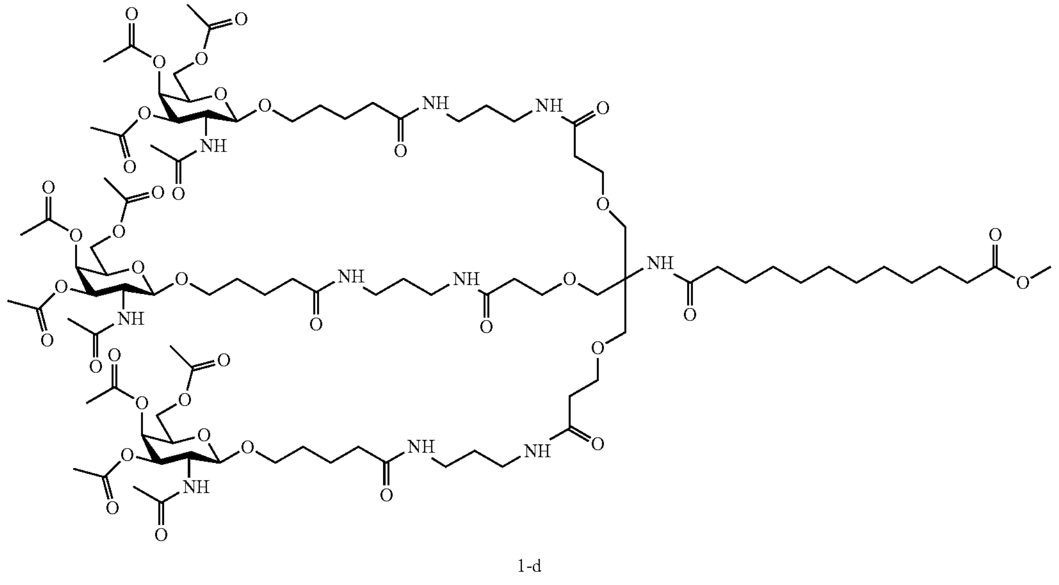
1-d

Compound 1-d was obtained as a white solid (1.5 g, 80%) according to the General procedure B starting from 1-b.
Step 3: Preparation of 11-{[1,3-bis(2-{[3-(5-{[4,5-bis(acetyloxy)-6-[(acetyloxy)methyl]-3-acetamidooxan-2-yl]oxy}pentanamido)propyl] carbamoyl}ethoxy)-2-[(2-{[3-(5-{[4,5-bis (acetyloxy)-6-[(acetyloxy)methyl]-3-acetamidooxan-2-yl]oxy}pentanamido)propyl] carbamoyl} ethoxy) methyl]propan-2-yl]carbamoyl}undecanoic acid (1-e)
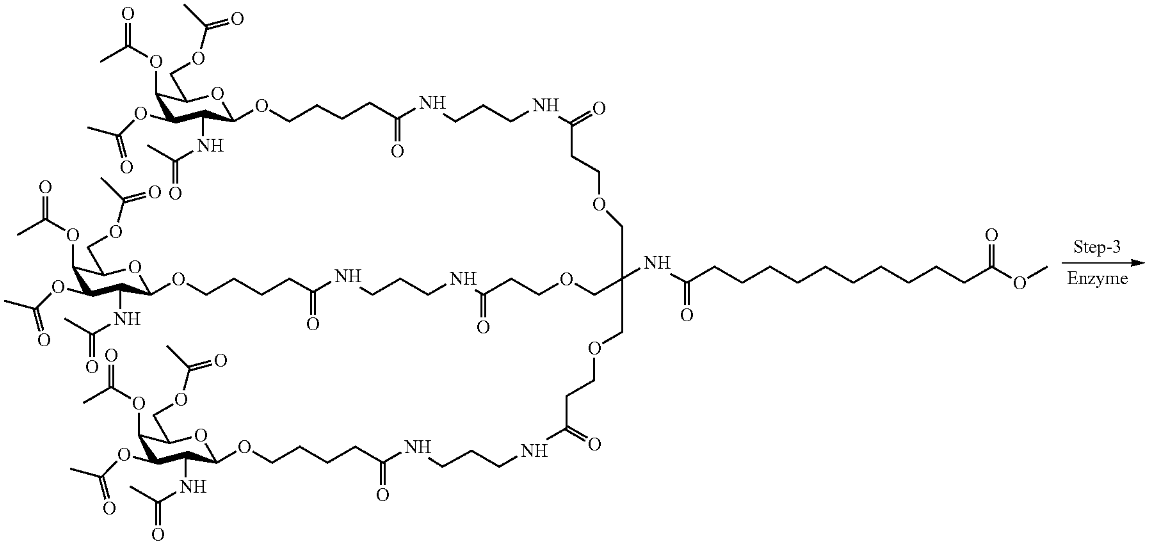
1-d
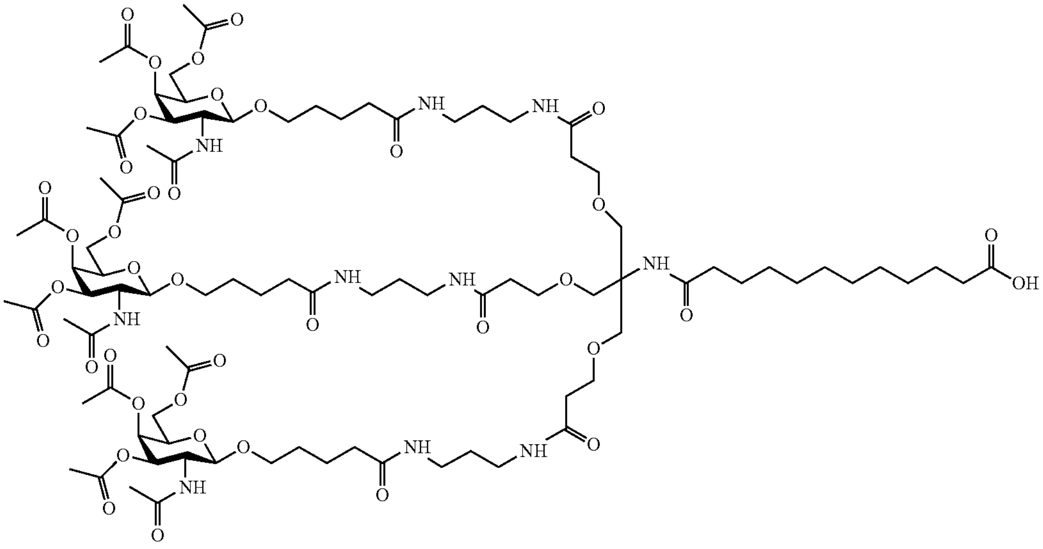
1-e Compound 1-e was obtained as an off-white foamy solid (25 g, 98%) according to General procedure C starting from 1-d.

Example-2

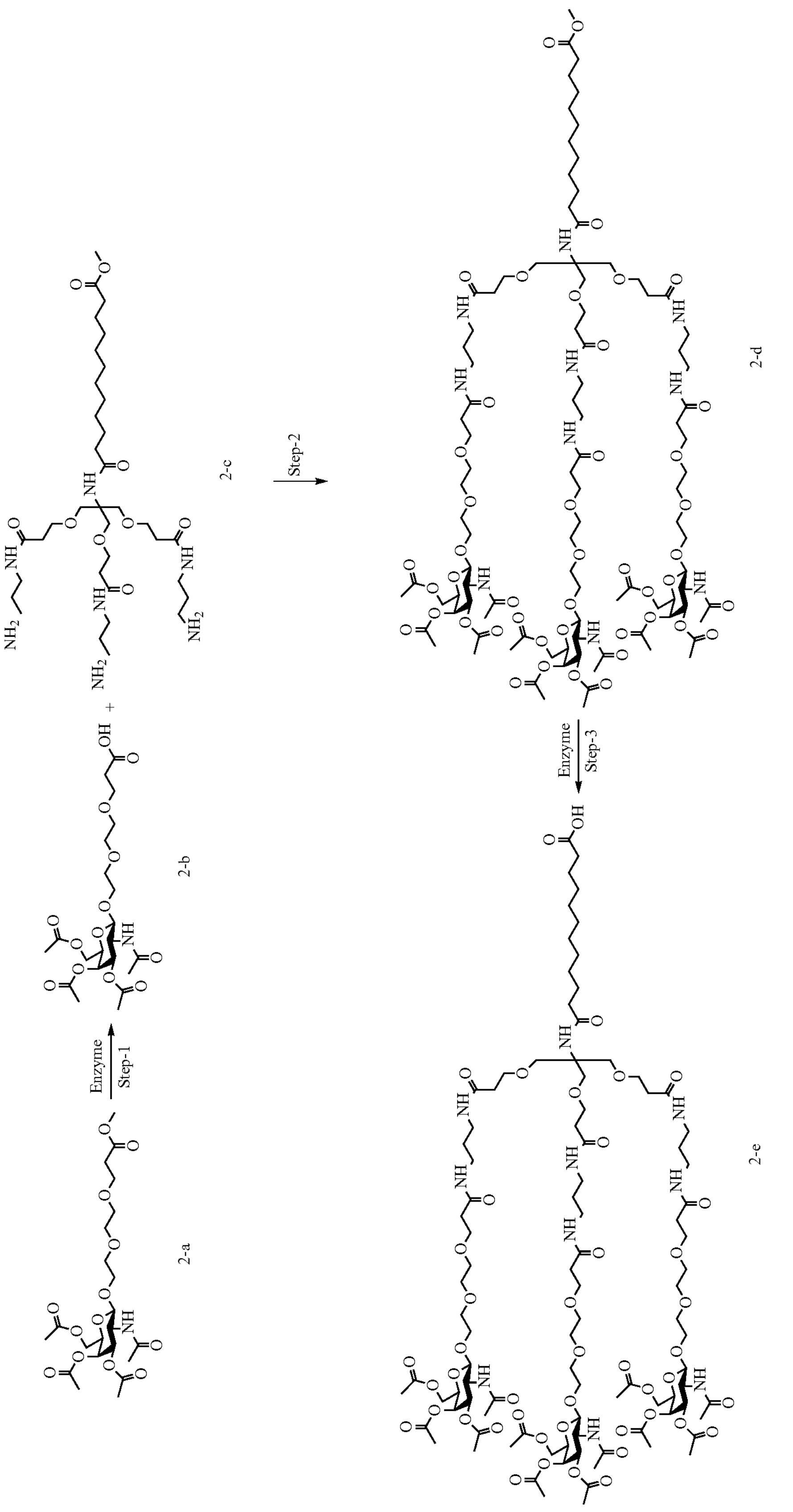
2-a
2-b
2-c
2-d
2-e

Step 1: Preparation of 3-[2-(2-{[(2R,5R)-4,5-bis(acetyloxy)-6-[(acetyloxy)methyl]-3-acetamidooxan-2-yl]oxy}ethoxy)ethoxy]propanoic acid (2-b)

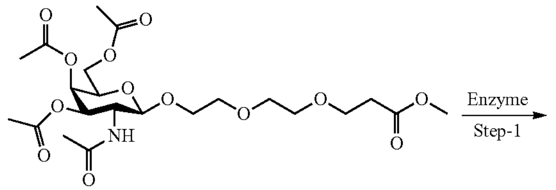

2-a

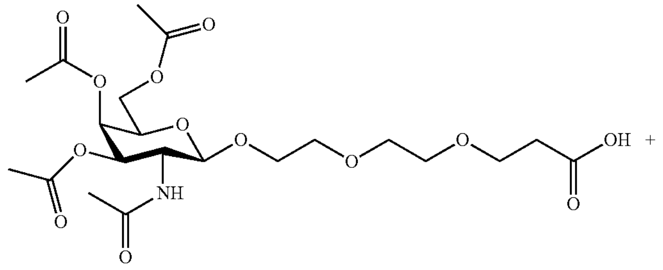

2-b

-continued

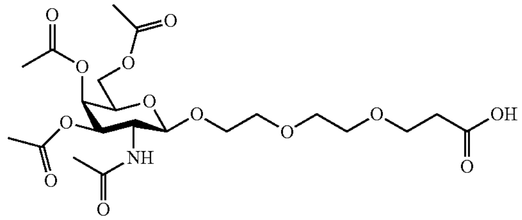

2-b

Compound 2-b was obtained as a white solid (1.0 g, 86%) according to the General procedure A starting from 2-a.

Step 2: Preparation of methyl 11-{[1,3-bis({2-[(3-{3-[2-(2-{[(2R,5R)-4,5-bis(acetyloxy)-6-[(acetyloxy)methyl]-3-acetamidooxan-2-yl]oxy}ethoxy)ethoxy]propanamido}propyl)carbamoyl]ethoxy})-2-({2-[(3-{3-[2-(2-{[(2R,5R)-4,5-bis(acetyloxy)-6-[(acetyloxy)methyl]-3-acetamidooxan-2-yl]oxy}ethoxy)ethoxy]propanamido}propyl)carbamoyl]ethoxy}methyl)propan-2-yl]carbamoyl}undecanoate (2-d)

-continued
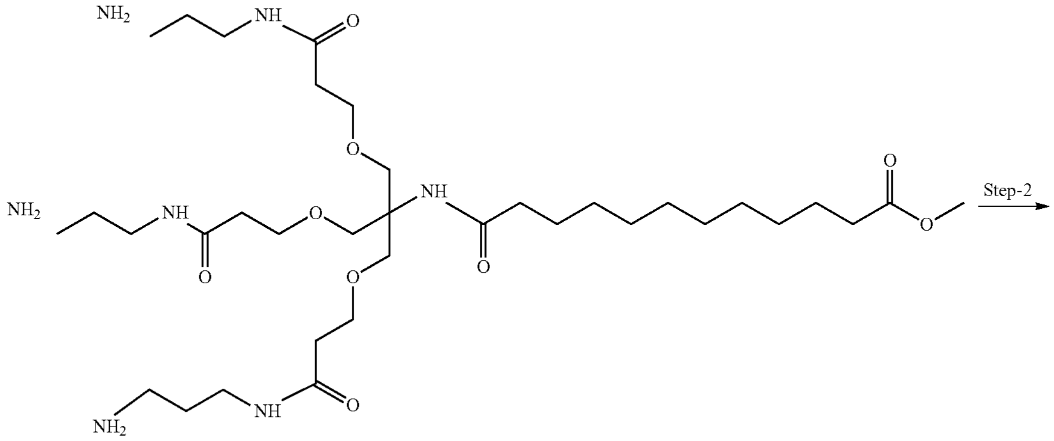
2-c
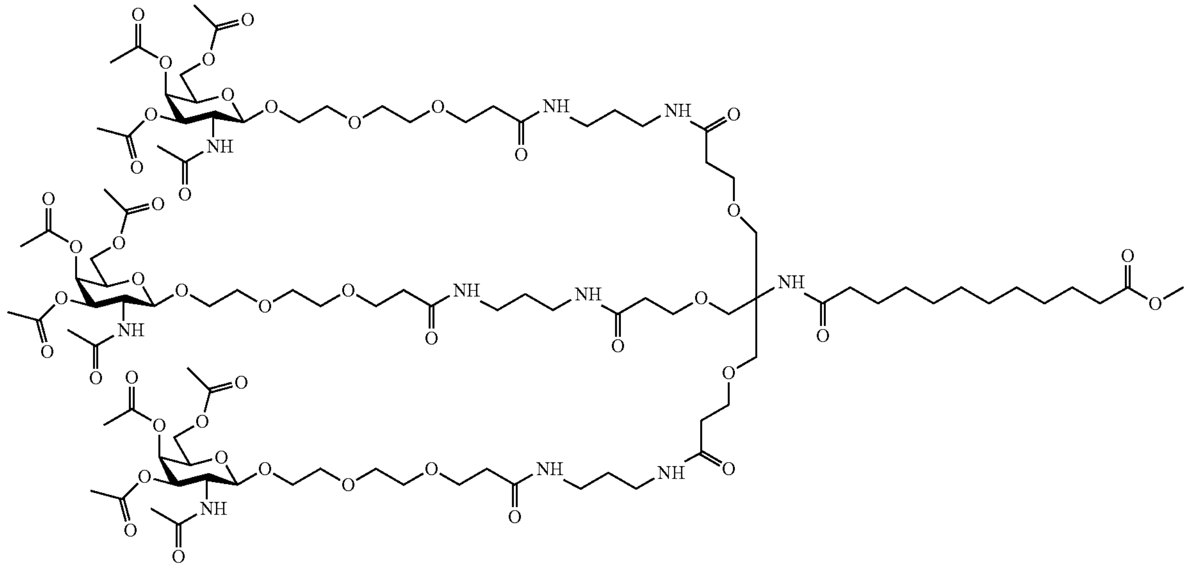
2-d

Compound 2-d was obtained as a white solid (1.7 g, 85%) according to the General procedure B starting from 2-a. under reduced pressure to afford 1.7 g (85%) of compound (2-d) as an off-white foam.

Step 3: Preparation of 11-{[1,3-bis({2-[(3-{3-[2-(2-{[(2R,5R)-4,5-bis(acetyloxy)-6-[(acetyloxy)methyl]-3-acetamidooxan-2-yl]oxy}ethoxy)ethoxy]propanamido}propyl)carbamoyl]ethoxy})-2-({2-[(3-{3-[2-(2-{[(2R,5R)-4,5-bis(acetyloxy)-6-[(acetyloxy)methyl]-3-acetamidooxan-2-yl]oxy}ethoxy)ethoxy]propanamido}propyl)carbamoyl]ethoxy}methyl)propan-2-yl]carbamoyl}undecanoic acid (2-e)

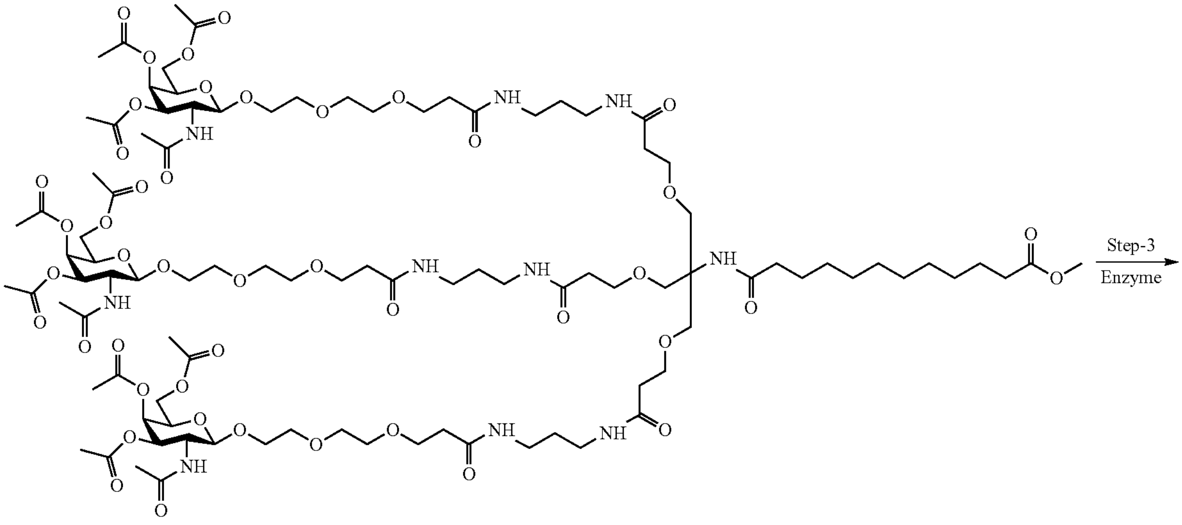

2-d

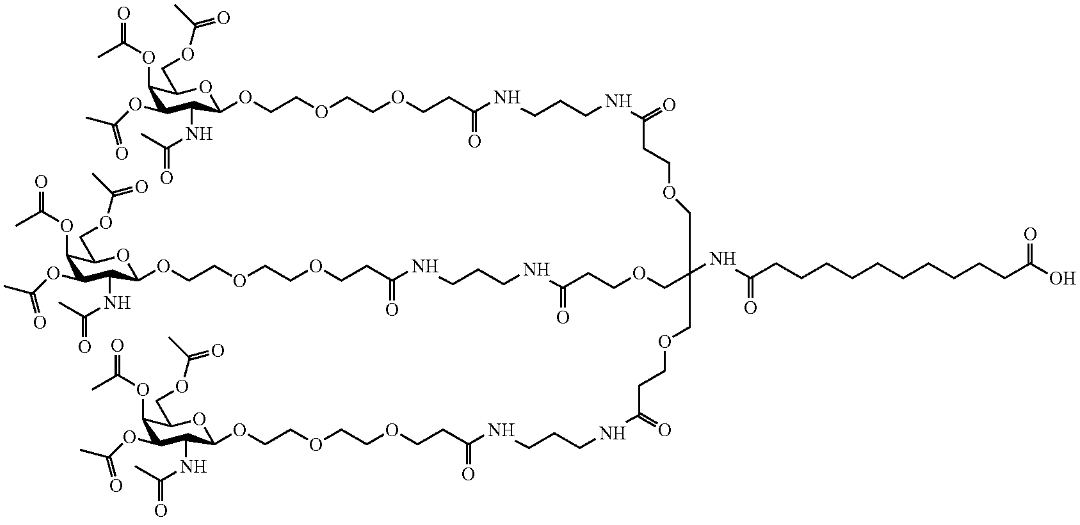

2-e

Compound 2-e was obtained as an off-white foamy solid (500 mg, 97%) according to the General procedure C starting from 2-d.

Example-3

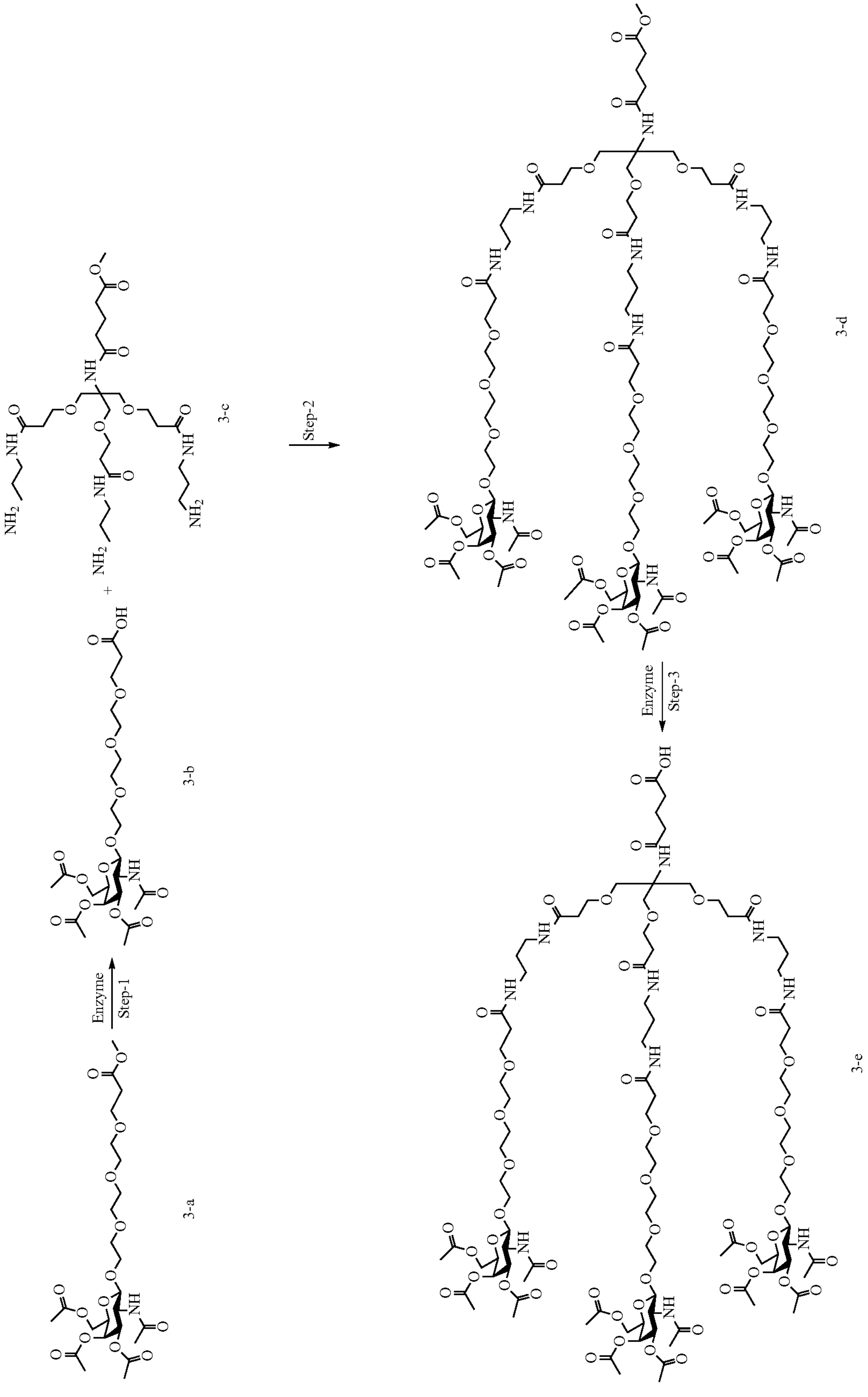
3-a 3-b 3-c 3-d 3-e

Step 1: Preparation of 3-{2-[2-(2-{[(2R,5R)-4,5-bis (acetyloxy)-6-[(acetyloxy)methyl]-3-acetamidooxan-2-yl]oxy}ethoxy)ethoxy]ethoxy}propanoic acid (3-b)

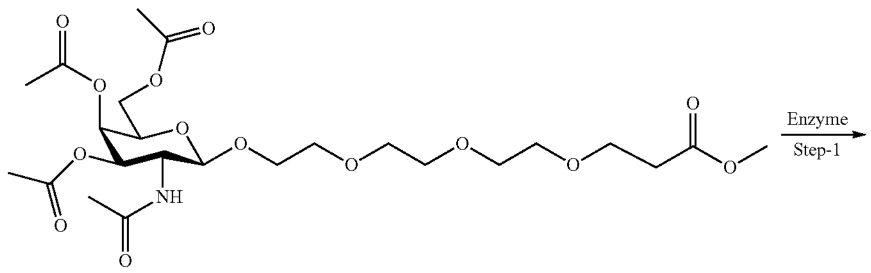

3-a

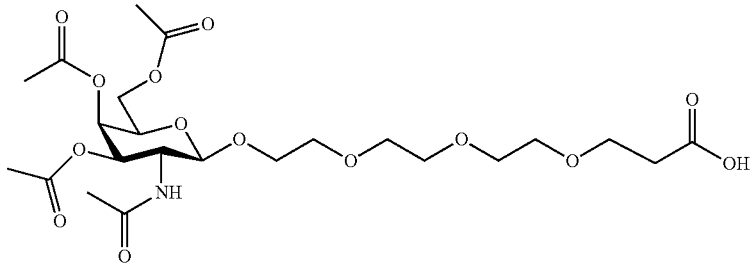

3-b

Compound 3-b was obtained as a white solid (2.0 g, 88%) according to the General procedure A starting from 3-a.

Step 2: Preparation of methyl 4-{[1-(2-{[3-(3-{2-[2-(2-{[(2R,5R)-5-(acetyloxy)-6-[(acetyloxy) methyl]-3-acetamido-4-(formyloxy)oxan-2-yl] oxy}ethoxy)ethoxy]ethoxy}propanamido)propyl] carbamoyl}ethoxy)-3-(2-{[3-(3-{2-[2-(2-{[(2R,5R)-4,5-bis(acetyloxy)-6-[(acetyloxy)methyl]-3-acetamidooxan-2-yl]oxy}ethoxy)ethoxy] ethoxy}propanamido)propyl]carbamoyl}ethoxy)-2-({2-[(3-{2-[2-(2-{[(2R,5R)-4,5-bis(acetyloxy)-6-[(acetyloxy)methyl]-3-acetamidooxan-2-yl] oxy}ethoxy)ethoxy]ethoxy} propanoyl)carbamoyl] ethoxy}methyl)propan-2-yl]carbamoyl}butanoate (3-d)

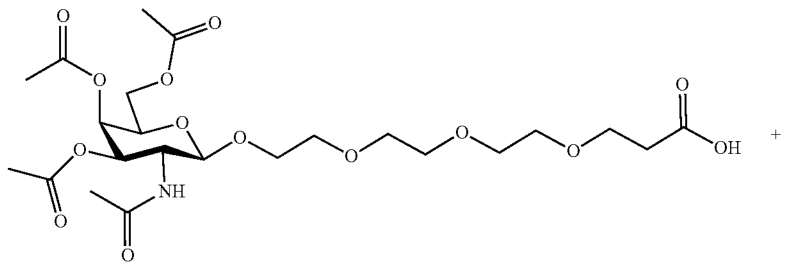

3-b

-continued
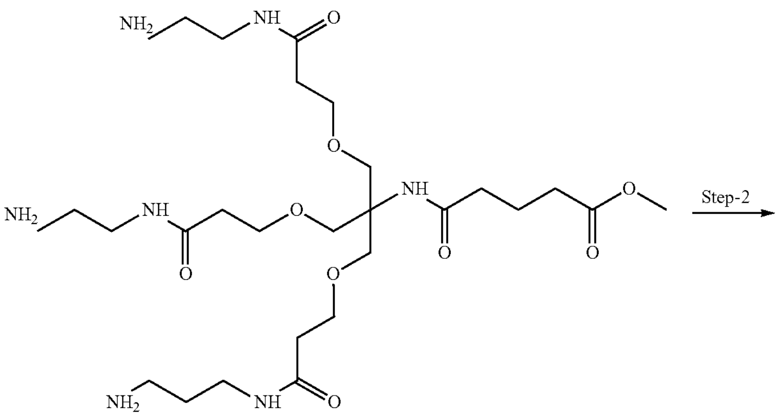
3-c
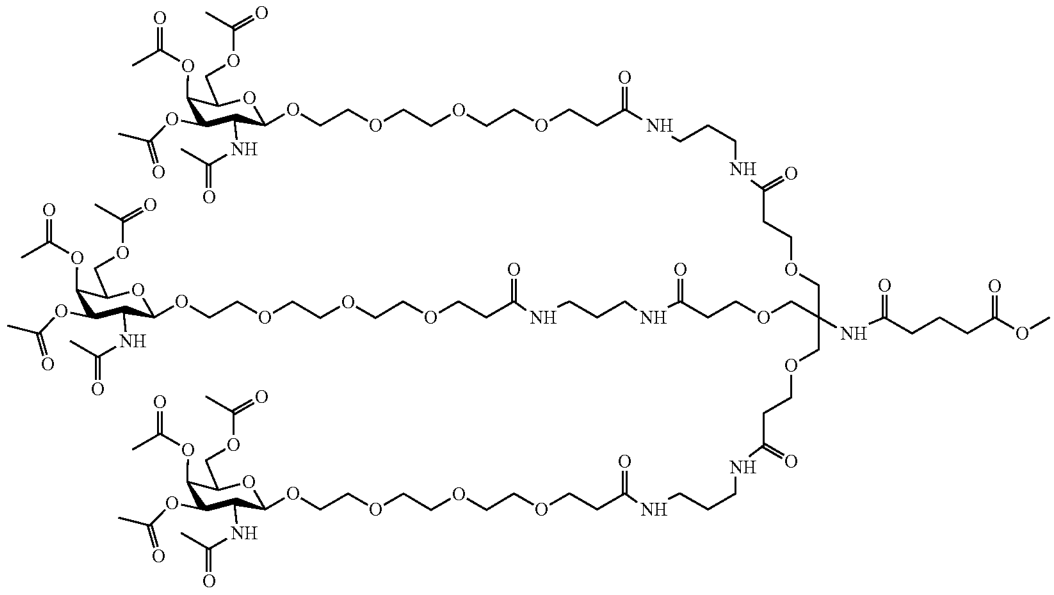
3-d

Compound 3-d was obtained as an off-white foam (4.0 g, 87%) according to the General procedure B starting from 3-b.

Step 3: Preparation of 4-{[1-(2-{[3-(3-{2-[2-(2-{[(2R,5R)-5-(acetyloxy)-6-[(acetyloxy)methyl]-3-acetamido-4-(formyloxy)oxan-2-yl]oxy}ethoxy)ethoxy]ethoxy}propanamido)propyl]carbamoyl}ethoxy)-3-(2-{[3-(3-{2-[2-(2-{[(2R,5R)-4,5-bis(acetyloxy)-6-[(acetyloxy)methyl]-3-acetamidooxan-2-yl]oxy}ethoxy)ethoxy]ethoxy}propanamido)propyl]carbamoyl}ethoxy)-2-({2-[(3-{2-[2-(2-{[(2R,5R)-4,5-bis(acetyloxy)-6-[(acetyloxy)methyl]-3-acetamidooxan-2-yl]oxy}ethoxy)ethoxy]ethoxy}propanoyl)carbamoyl]ethoxy}methyl)propan-2-yl]carbamoyl}butanoic acid (3-e)

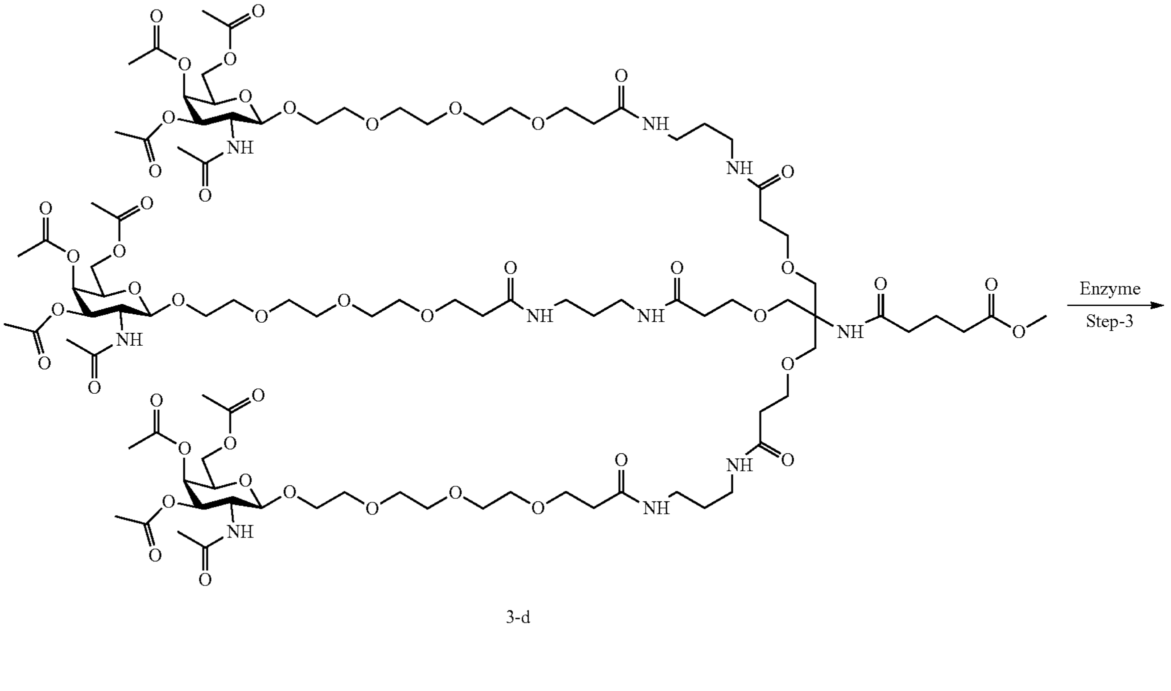

3-d

-continued
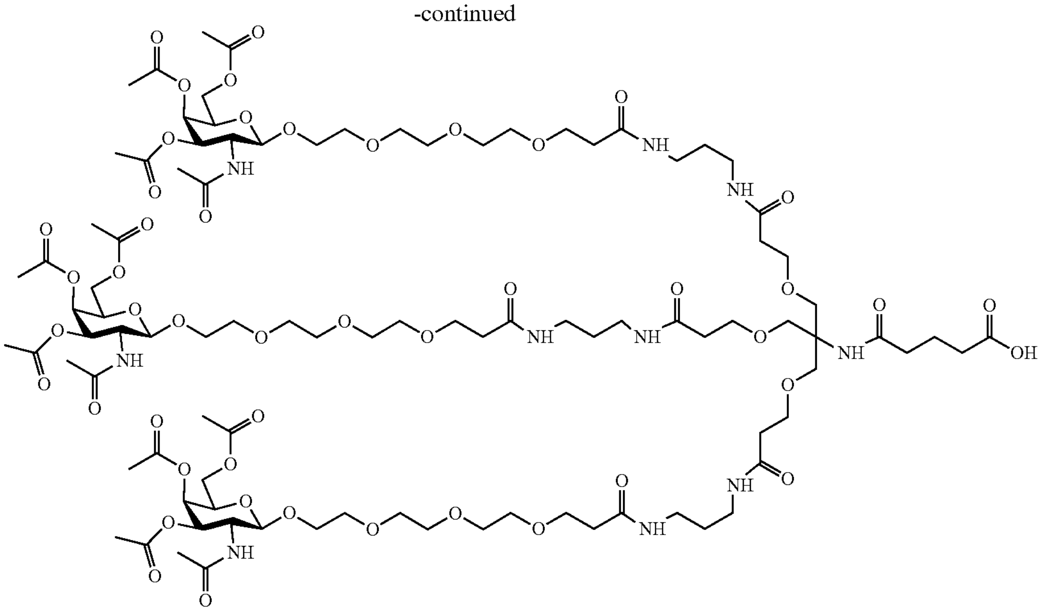
3-e
Compound 3-e was obtained as an off-white foamy solid (1.5 g, 96%) according to the General procedure C starting from 3-d.
Example-4
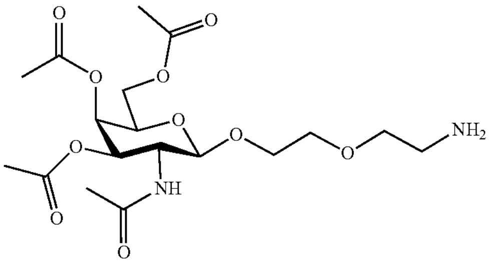
+
4-a
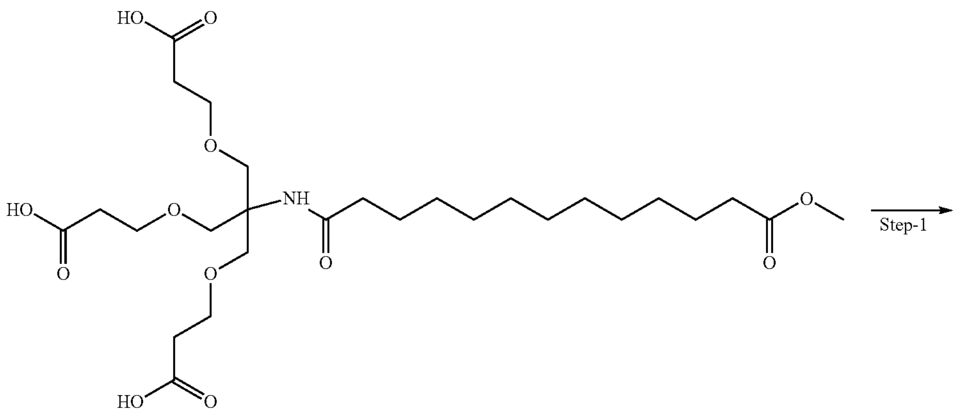
4-b -continued
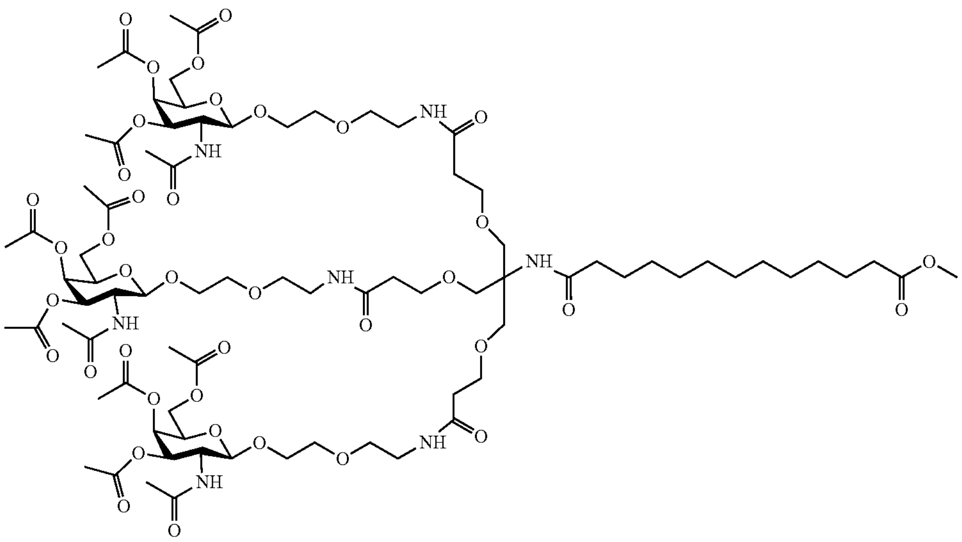
4-c
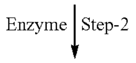
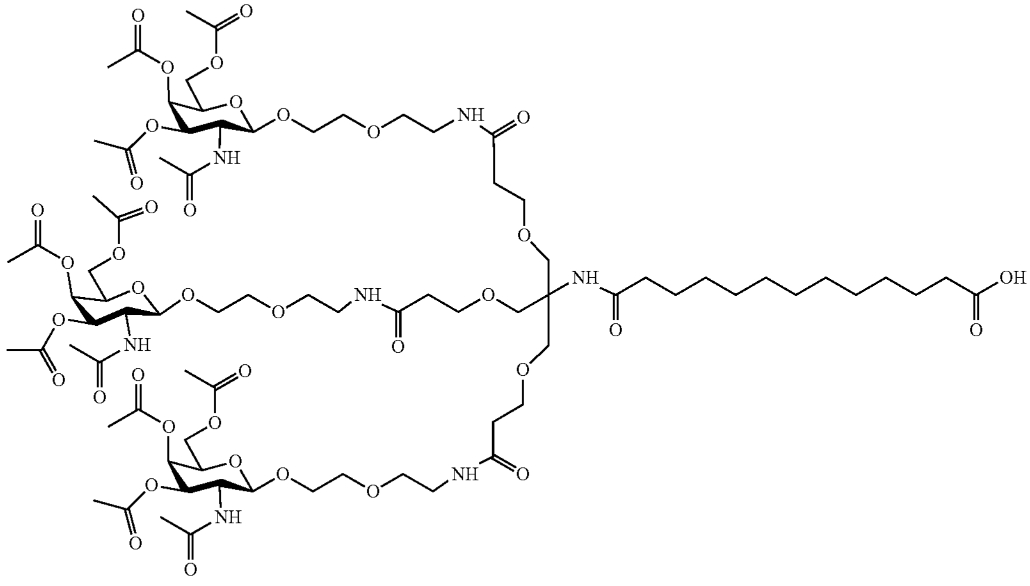
4-d Step 1: Preparation of methyl 12-{[1,3-bis(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethoxy)-2-[(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethoxy)methyl]propan-2-yl]carbamoyl}dodecanoate (4-c)
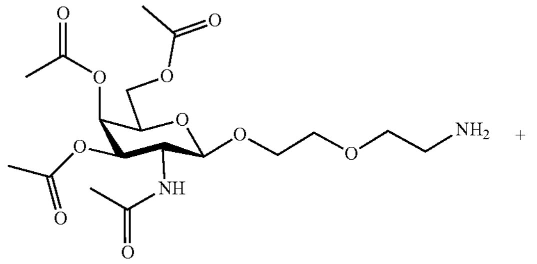
4-a
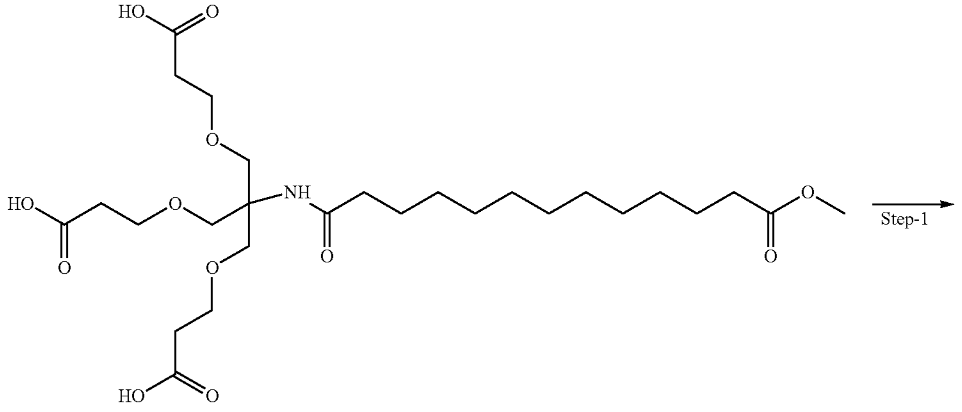
4-b
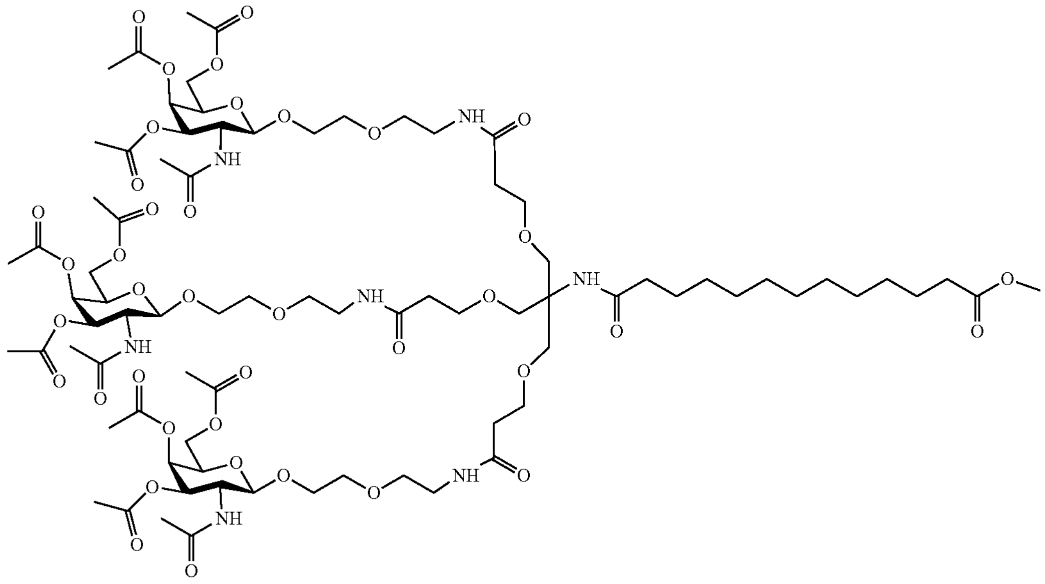
4-c Compound 4-c was obtained as an off-white foamy solid (3.5 g, 94%) according to the General procedure B starting from 4-a.
Step 2: Preparation of 12-{[1,3-bis(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethoxy)-2-[(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethoxy)methyl]propan-2-yl]carbamoyl}dodecanoic acid (4-d)
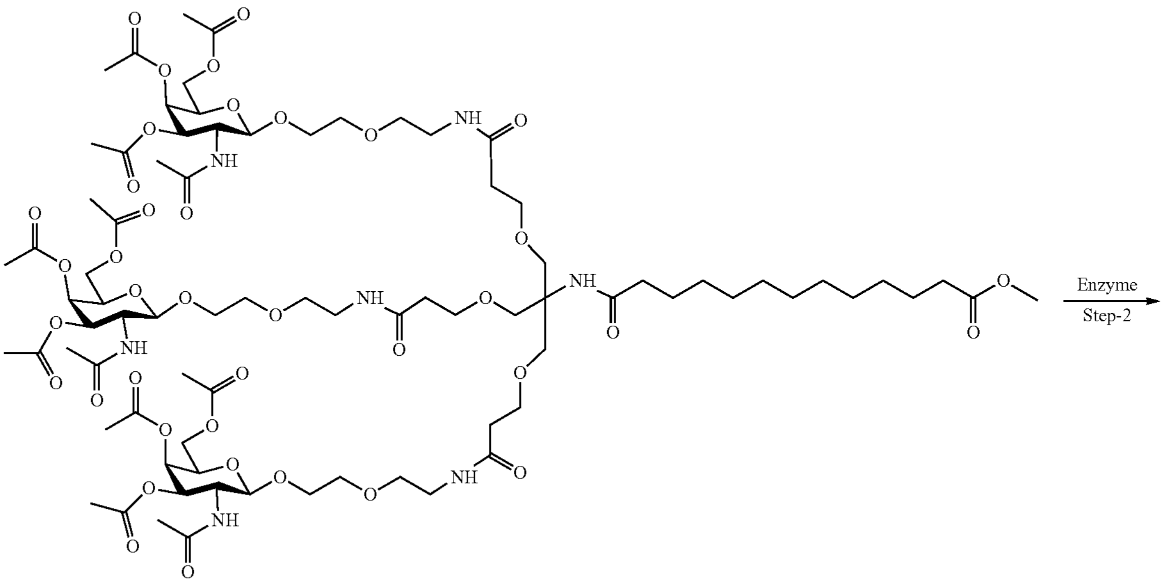
4-c
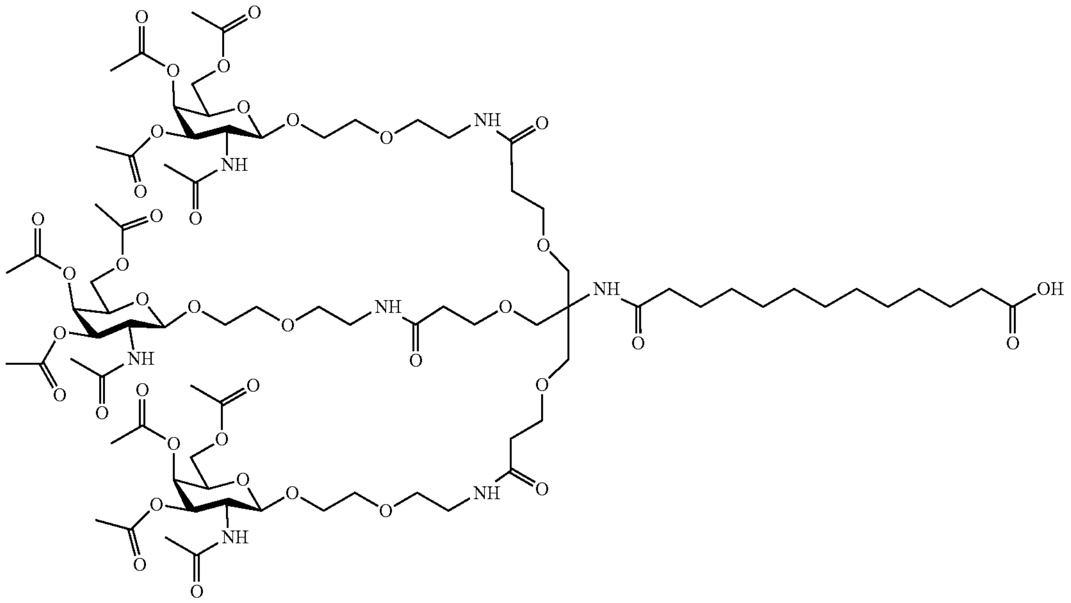
4-d Compound 4-d was obtained as an off-white foamy solid (1.8 g, 99%) according to the General procedure C starting from 4-c.
Example-5
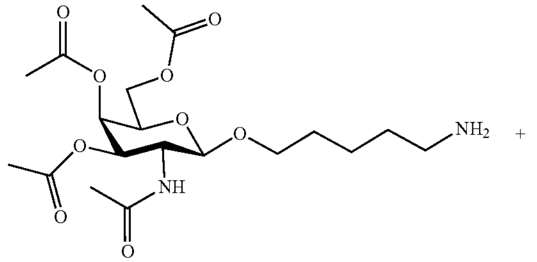
5-a
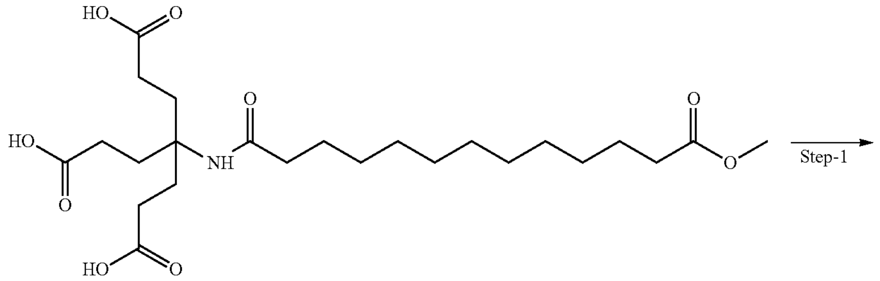
5-b
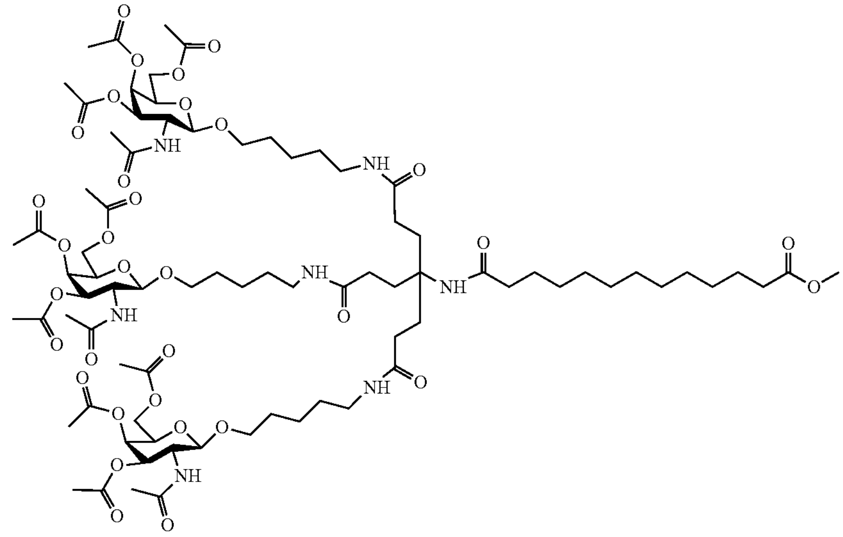
5-c
Enzyme Step-2

-continued
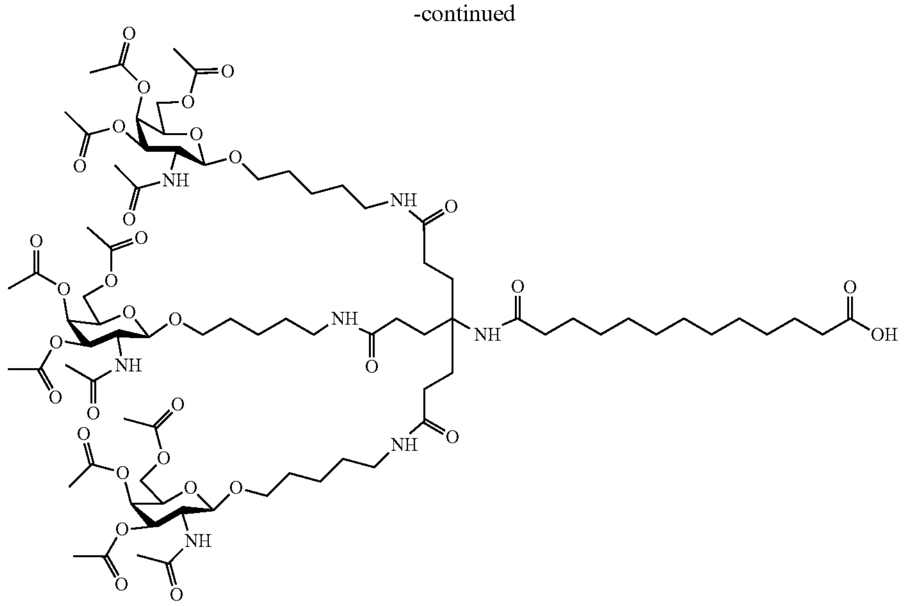
5-d
Step 1: Preparation of methyl 12-({1,5-bis[(5-{[(2R,5R)-4,5-bis(acetyloxy)-6-[(acetyloxy)methyl]-3-acetamidooxan-2-yl]oxy}pentyl)carbamoyl]-3-{2-[(5-{[(2R,5R)-4,5-bis(acetyloxy)-6-[(acetyloxy)methyl]-3-acetamidooxan-2-yl]oxy}pentyl)carbamoyl]ethyl}pentan-3-yl}carbamoyl)dodecanoate (5-c)
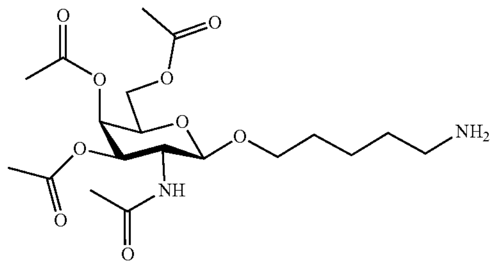
+
5-a -continued
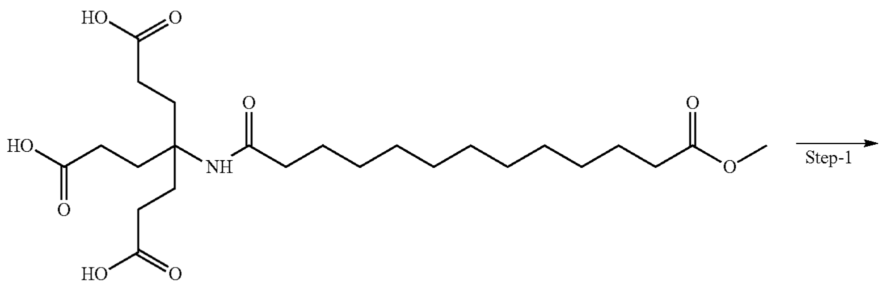
5-b
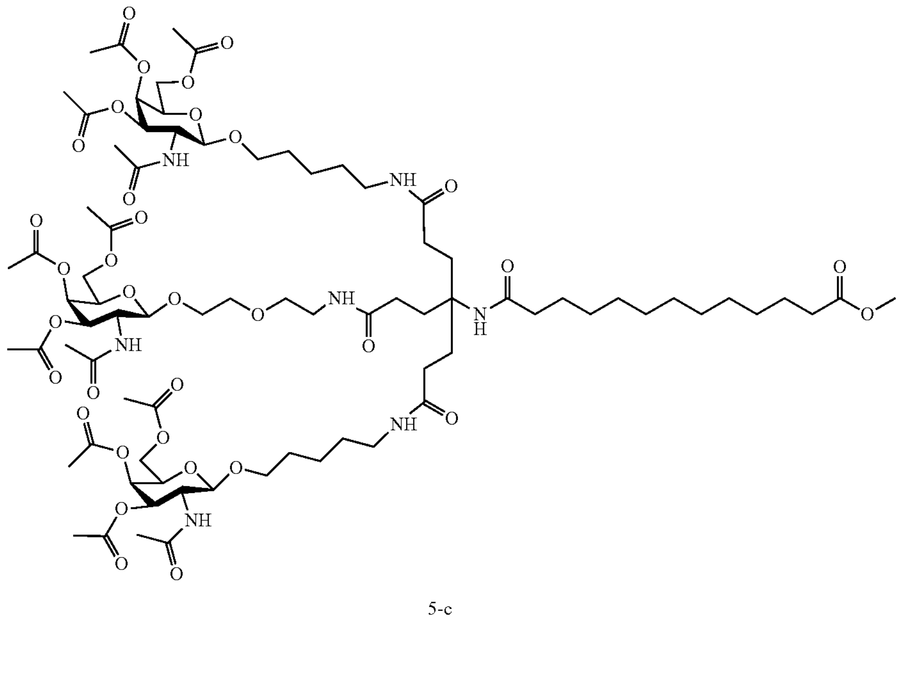
5-c Compound 5-c was obtained as an off-white foamy solid (4.0 g, 98%) according to the General procedure B starting from 5-a.
Step 2: Preparation of 12-({1,5-bis[(5-{[(2R,5R)-4,5-bis(acetyloxy)-6-[(acetyloxy)methyl]-3-acetamidooxan-2-yl]oxy}pentyl)carbamoyl]-3-{2-[(5-{[(2R,5R)-4,5-bis(acetyloxy)-6-[(acetyloxy)methyl]-3-acetamidooxan-2-yl]oxy}pentyl)carbamoyl]ethyl}pentan-3-yl}carbamoyl)dodecanoic acid (5-d)
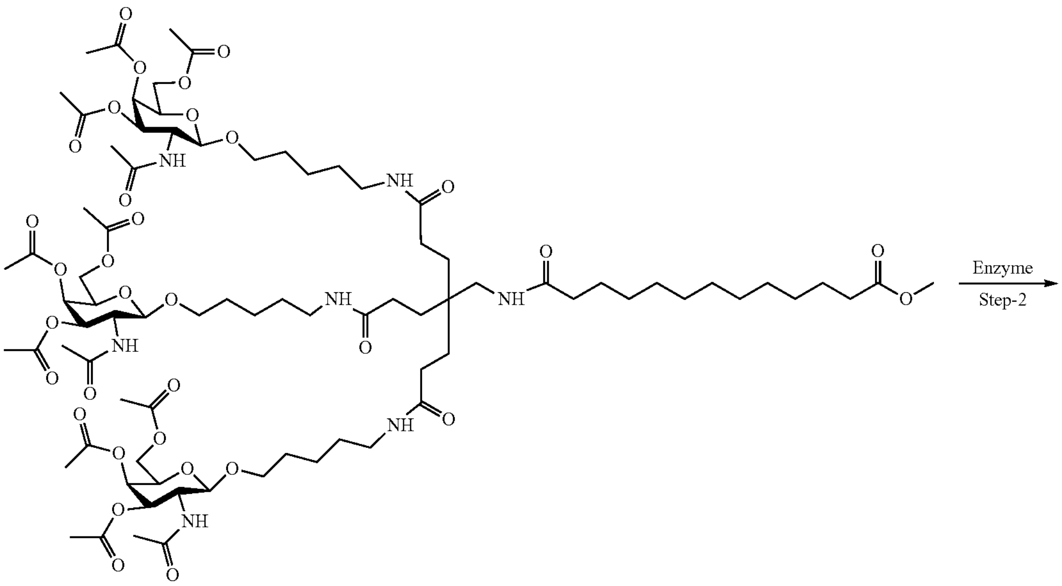
5-c
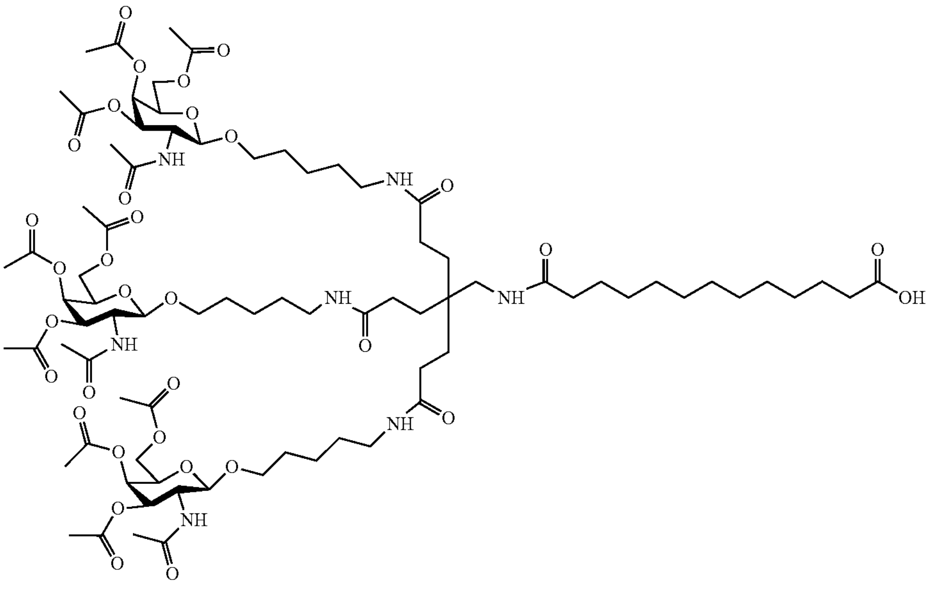
5-d Compound 5-d was obtained as an off-white foamy solid (1.5 g, 95%) according to the General procedure C starting from 5-c.

Example-6

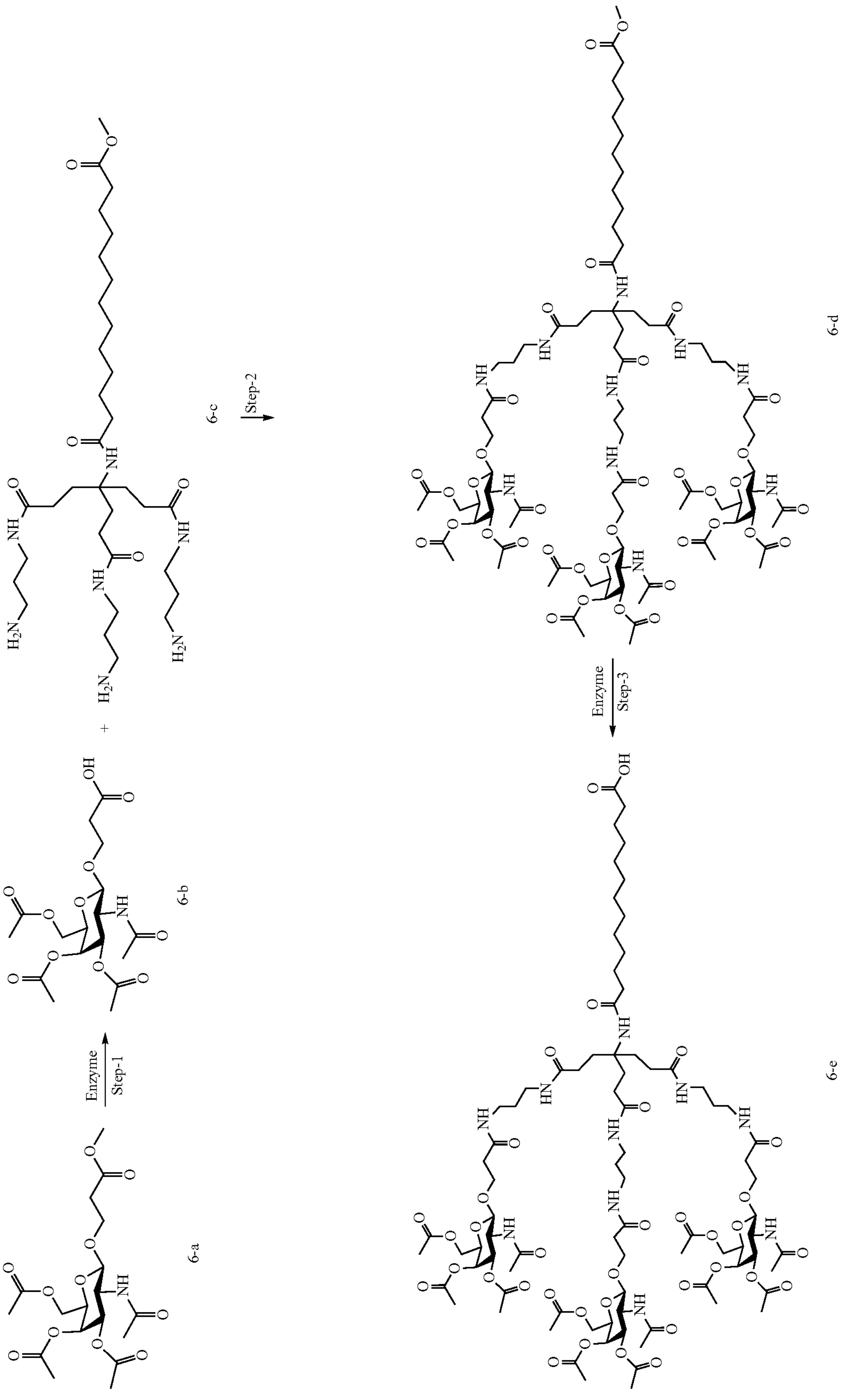
6-a
6-b
6-c
6-d
6-e

Step 1: Preparation of 3-{[(2R,5R)-4,5-bis(acetyloxy)-6-[(acetyloxy)methyl]-3-acetamidooxan-2-yl]oxy}propanoic acid (6-b)

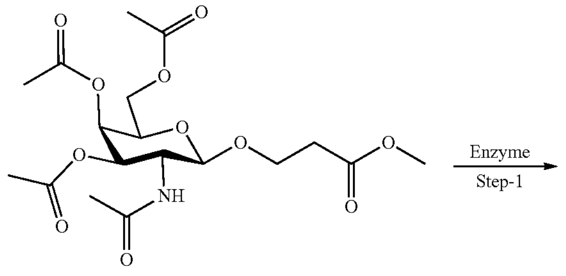

6-a

-continued

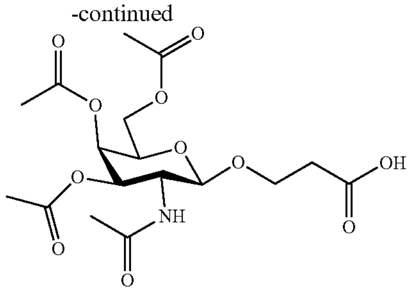

6-b

Compound 6-b was obtained as a white solid (10 g, 90%) according to the General procedure A starting from 6-a.

Step 2: Preparation of methyl 12-{[1,5-bis({[3-(3-{[(2R,5R)-4,5-bis(acetyloxy)-6-[(acetyloxy)methyl]-3-acetamidooxan-2-yl]oxy}propanamido)propyl]carbamoyl})-3-(2-{[3-(3-{[(2R,5R)-4,5-bis(acetyloxy)-6-[(acetyloxy)methyl]-3-acetamidooxan-2-yl]oxy}propanamido)propyl]carbamoyl}ethyl)pentan-3-yl]carbamoyl}dodecanoate (6-d)

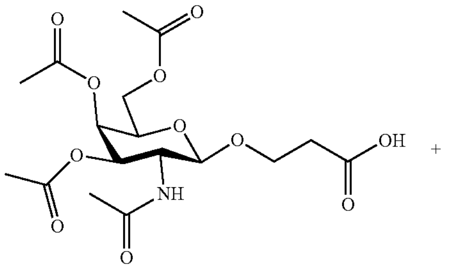

6-b

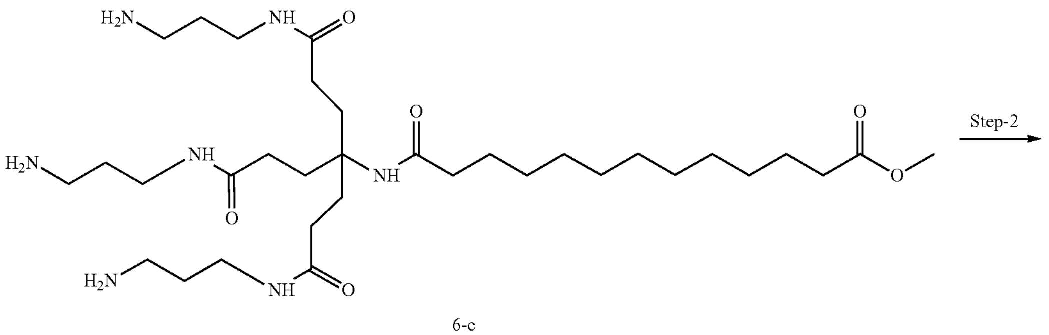

6-c

-continued
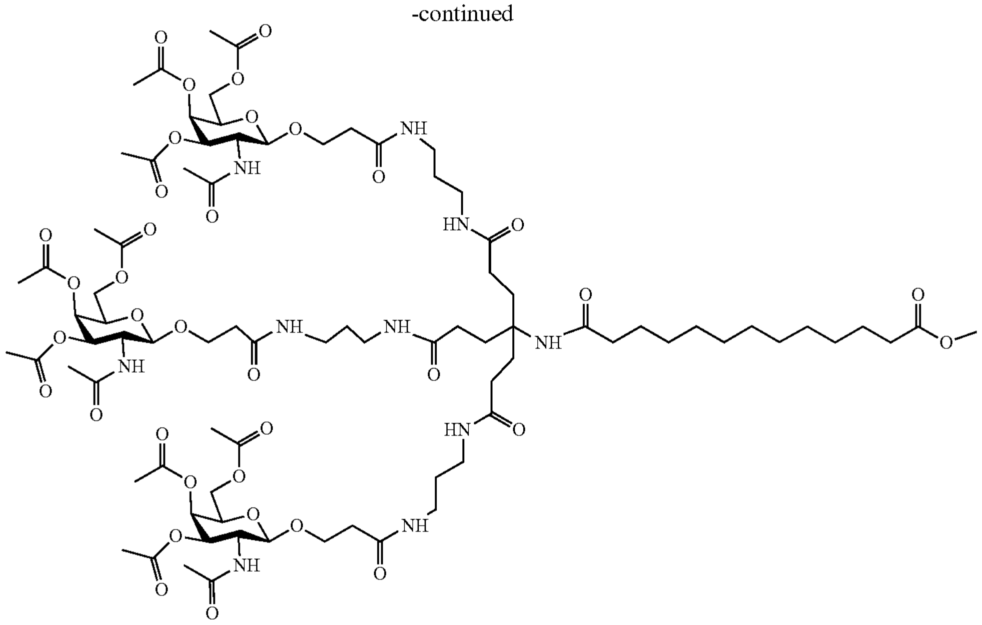
6-d
Compound 6-d was obtained as a white solid (2.5 g, 82%) according to the General procedure B starting from 6-b.
Step 3: Preparation of 12-{[1,5-bis({[3-(3-{[(2R,5R)-4,5-bis(acetyloxy)-6-[(acetyloxy)methyl]-3-acetamidooxan-2-yl]oxy}propanamido)propyl]carbamoyl})-3-(2-{[3-(3-{[(2R,5R)-4,5-bis(acetyloxy)-6-[(acetyloxy)methyl]-3-acetamidooxan-2-yl]oxy}propanamido)propyl]carbamoyl}ethyl)pentan-3-yl]carbamoyl}dodecanoic acid (6-e)
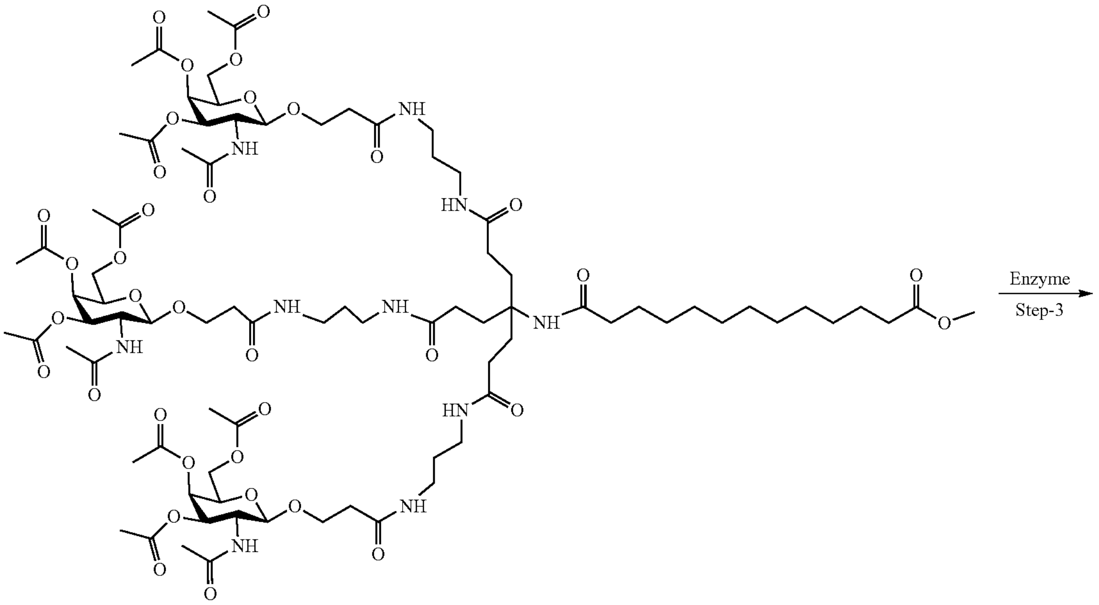
6-d -continued
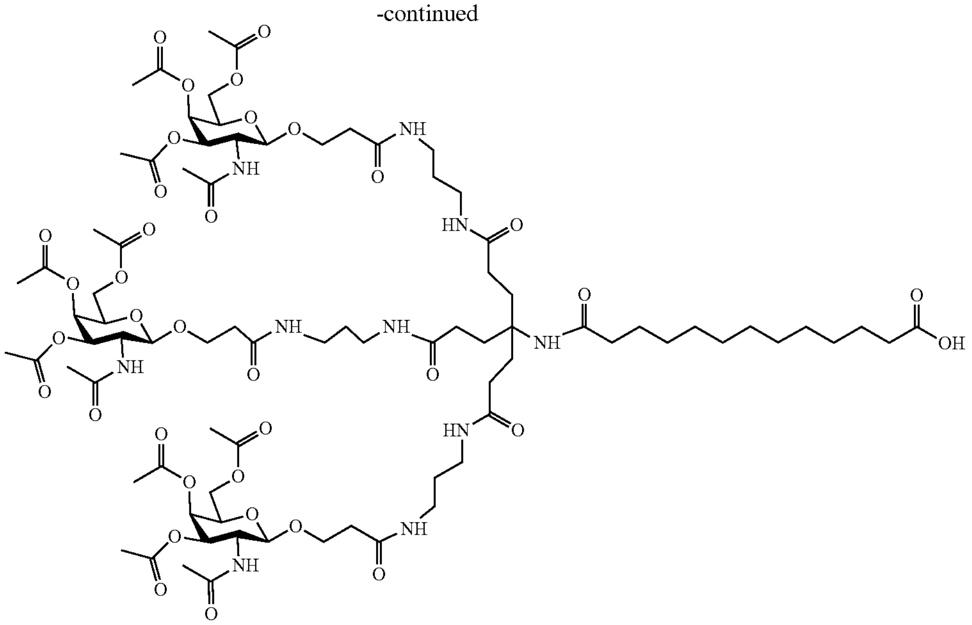
6-e
Compound 6-e was obtained as an off-white foamy solid (0.8 g, 94%) according to General procedure C starting from 6-d.
Example-7
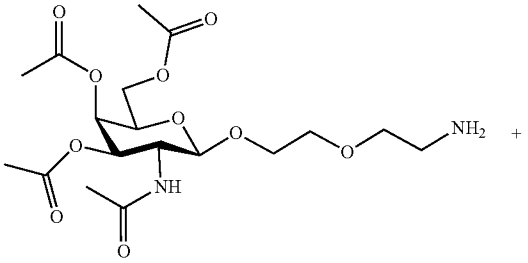
7-a
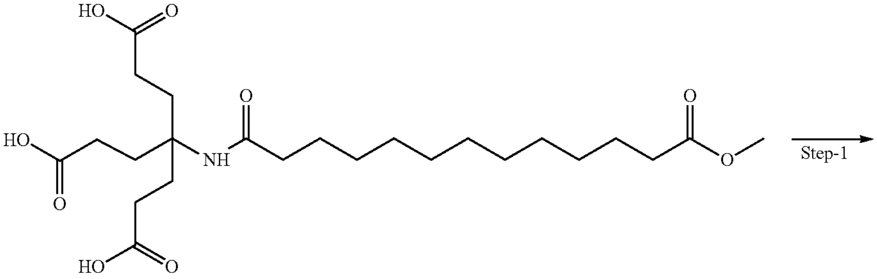
7-b -continued
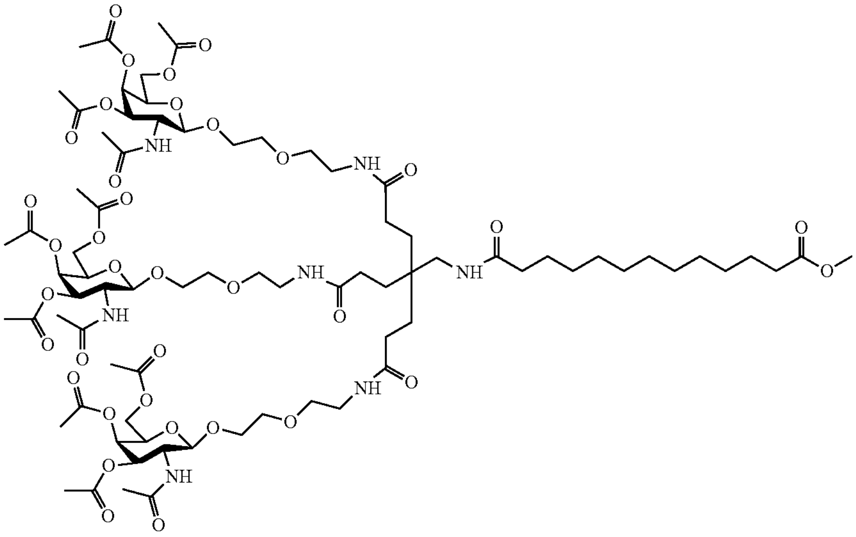
7-c
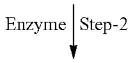
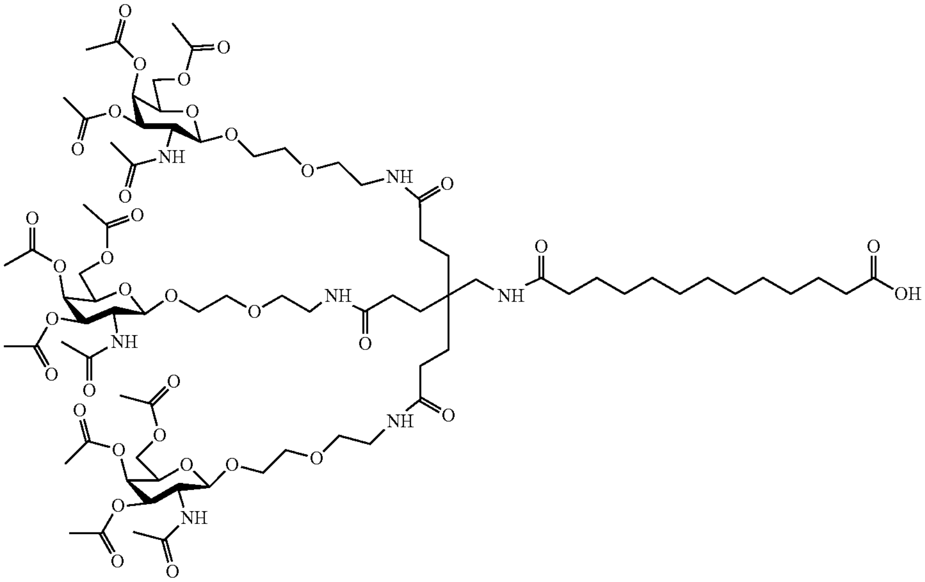
7-d Step 1: Preparation of methyl 12-{[1,5-bis({[2-(2-{[(2R,5R)-4,5-bis(acetyloxy)-6-[(acetyloxy)methyl]-3-acetamidooxan-2-yl]oxy}ethoxy)ethyl]carbamoyl})-3-(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethyl)pentan-3-yl]carbamoyl}dodecanoate (7-c)
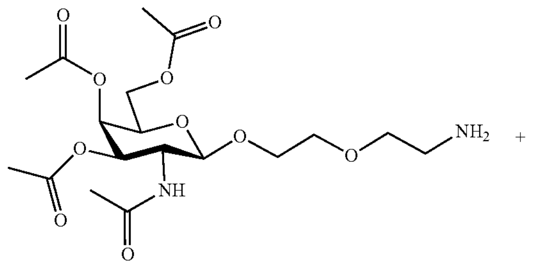
7-a
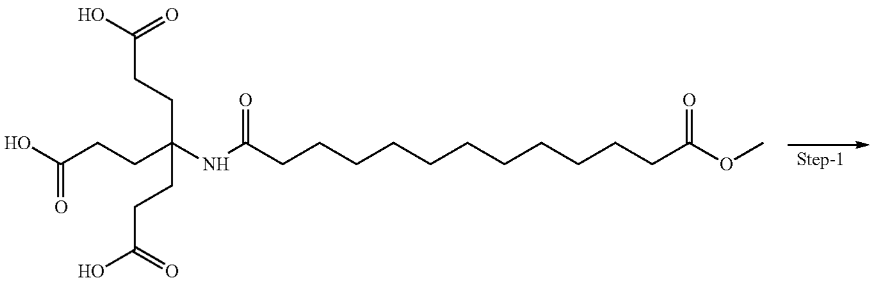
7-b
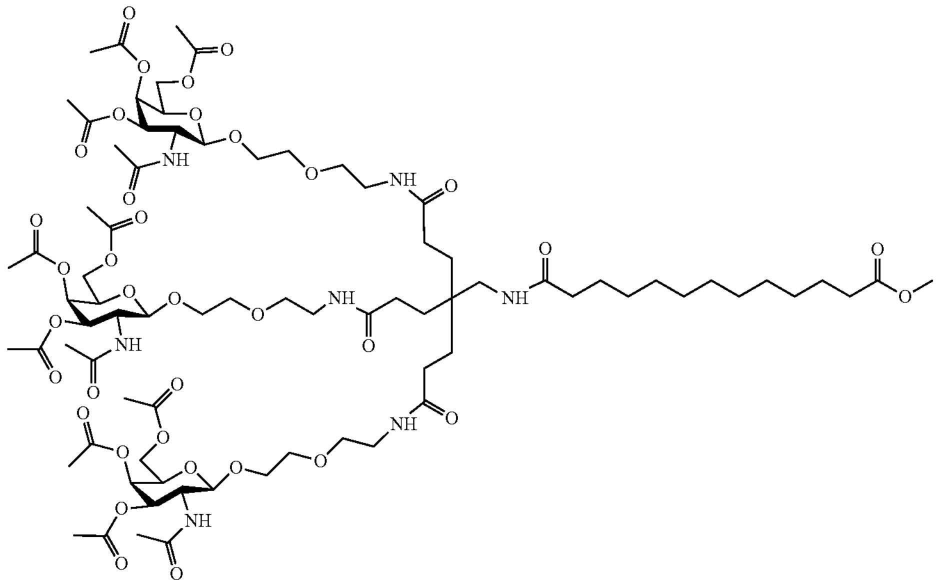
7-c Compound 7-c was obtained as an off-white foamy solid (20.0 g, 93%) according to the General procedure B starting from 7-a.
Step 2: Preparation of 12-{[1,5-bis({[2-(2-{[(2R,5R)-4,5-bis(acetyloxy)-6-[(acetyloxy)methyl]-3-acetamidooxan-2-yl]oxy}ethoxy)ethyl]carbamoyl})-3-(2-{[2-(2-{[(2R,5R)-4,5-bis(acetyloxy)-6-[(acetyloxy)methyl]-3-acetamidooxan-2-yl]oxy}ethoxy)ethyl]carbamoyl}ethyl)pentan-3-yl]carbamoyl}dodecanoic acid (7-d)
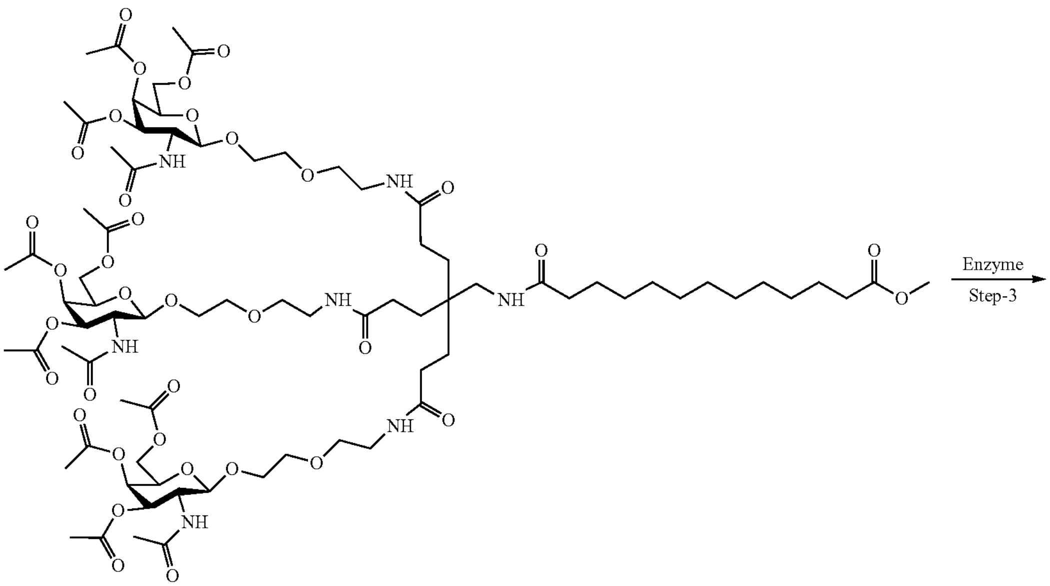
7-c
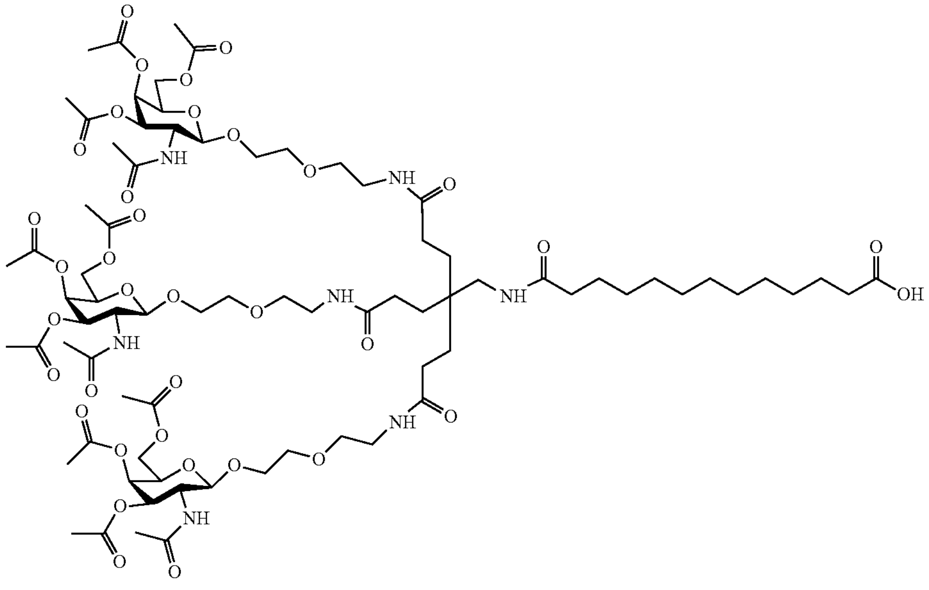
7-d Compound 7-d was obtained as an off-white foamy solid (15 g, 94%) according to the General procedure C starting from 7-c.

Thus, the present invention provides a facile method through selective hydrolysis of preparation of Glycolipid carboxylic acids in high yield by environmentally benign approach using simple reagents.

It is to be understood that the present invention is susceptible to modifications, changes and adaptations by those skilled in the art. Such modifications, changes, adaptations are intended to be within the scope of the present invention.

The invention claimed is:

1. A process for preparing compounds of Formula (I)

Formula I

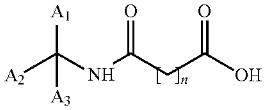

wherein:

"n" ranges from 1-15;

A1, A2 and A3 are each independently selected from H or

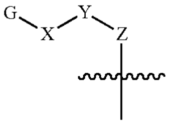

Provided that A1, A2 and A3 together are not H;

G is selected from the following groups:

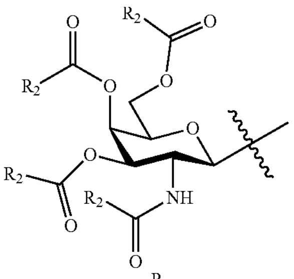

or

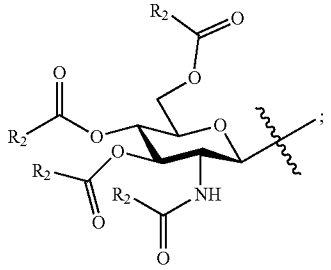

X is selected from the following groups:

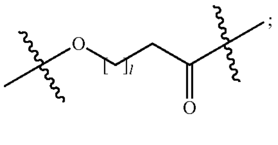

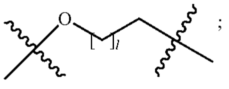

-continued

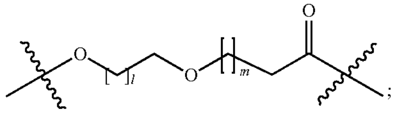

or

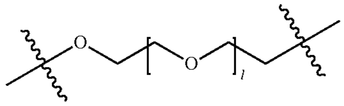

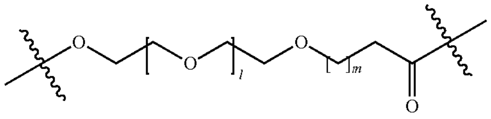

Y is selected from the following groups:

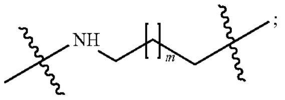

and —NH—;

Z is selected from the following groups:

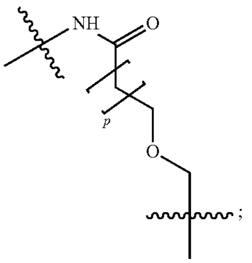

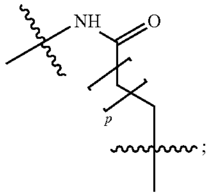

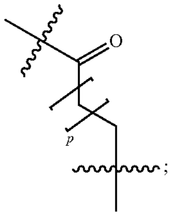

or

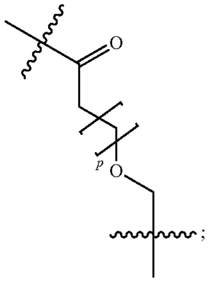

Wherein $R_2$ is selected from alkyl, aryl, alkoxy, aryloxy or arylalkyl groups;

"l" and "p" each independently ranges from 0-15;

Comprising the step of:

(a) Subjecting the compound of Formula (Ia)

Formula Ia

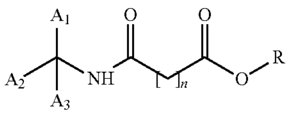

wherein R is selected from alkyl, aryl or aralkyl groups to hydrolysis in the presence of enzyme, selected from lipases, protease, amylase, trypsin, papain or combinations thereof, and water;

(b). Stirring the reaction mixture of step (a) followed by concentrating, drying and dilution with solvent;

(c) Removal of the enzyme solid precipitate from the reaction mixture of step (b) followed by purification to obtain compounds of Formula (I).

2. The process according to claim 1, wherein $A_1$, $A_2$ and $A_3$ is each independently

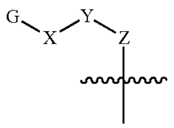

and the substituent

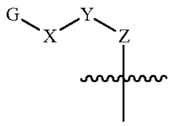

is selected from the following groups:

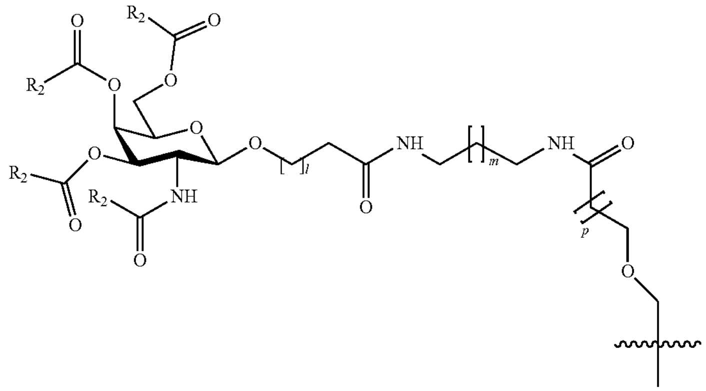

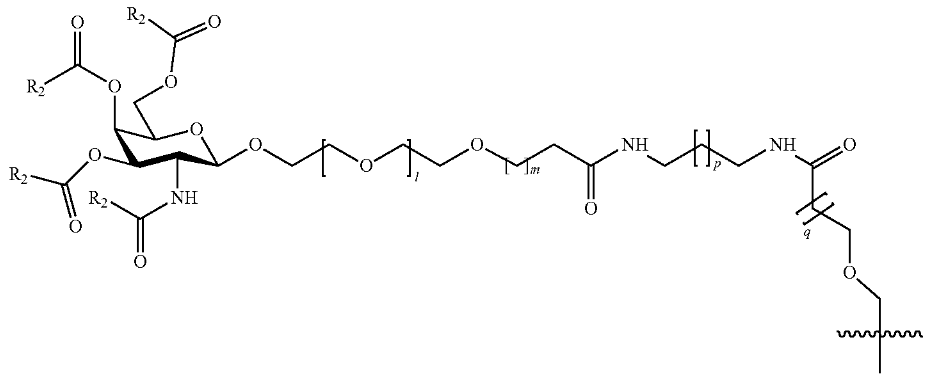

-continued
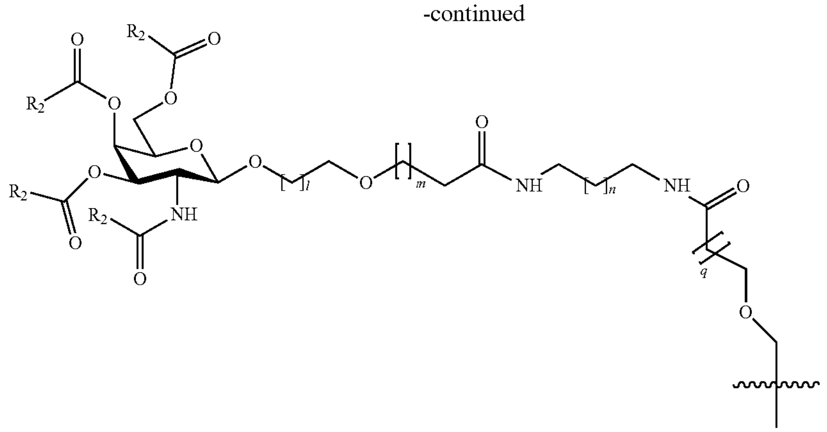
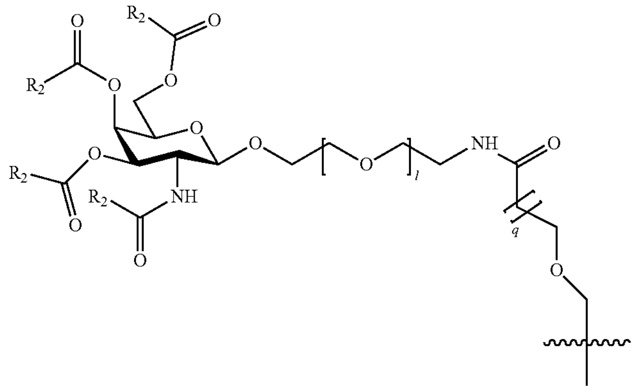
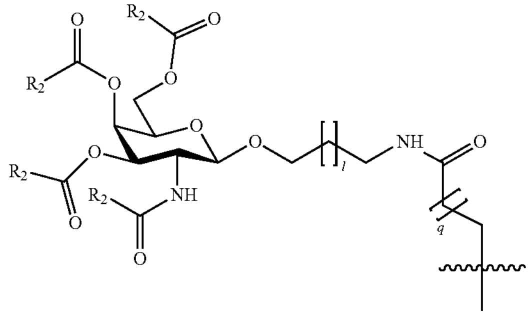

-continued

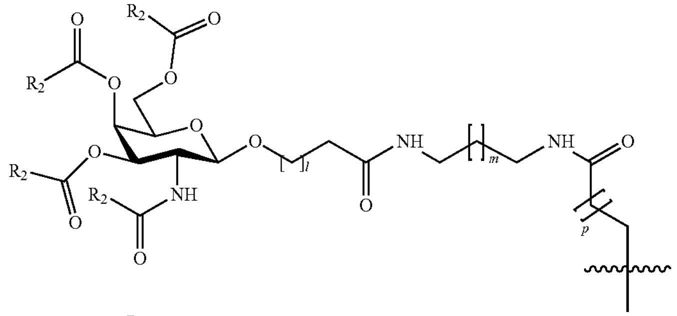

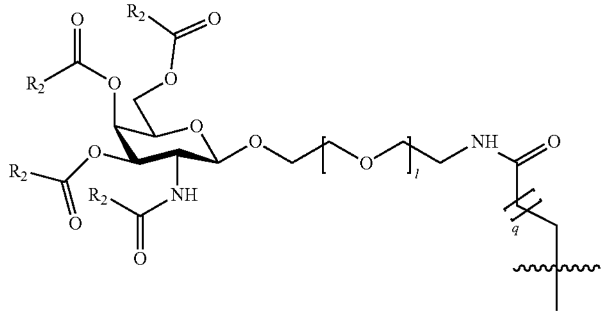

Wherein $R_2$ is selected from alkyl, aryl, alkoxy, aryloxy or arylalkyl groups;

"l", "m", "n" and "p" and "q" each independently ranges from 0-15.

3. The process according to claim 1, wherein the enzyme at step (a) is present in an amount ranging from 1 to 100% by weight of glycolipid esters of Formula (Ia).

4. The process according to claim 1, wherein the enzymatic hydrolysis at step (a) is carried out for 1-48 hrs at 20-45° C.

5. The process according to claim 1, wherein the solvent at step (b) is selected from water, methanol, ethanol isopropyl alcohol Methyl tert-butyl ether, dichloromethane, ethyl acetate, acetone, dimethyl formamide, tetrahydrofuran and acetonitrile or combinations thereof.

6. A process for preparing compounds of Formula (I'):

Formula (I')

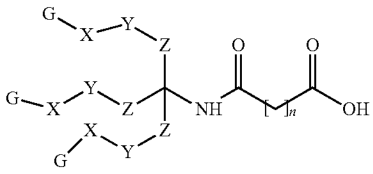

Wherein:

"n" ranges from 1-15;

Wherein G is selected from the following groups:

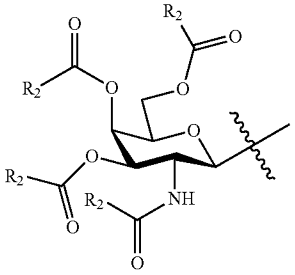

or

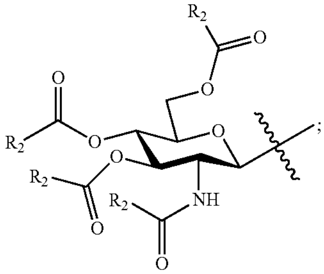

;

X is selected from the following groups:

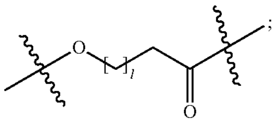

;

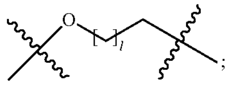

;

-continued

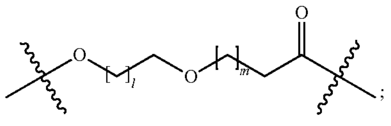

or Y is selected from the following groups:

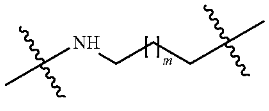

and —NH—;

Z is selected from the following groups:

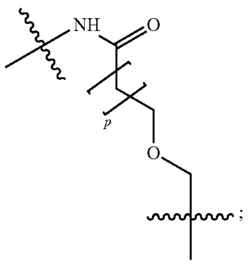

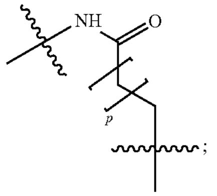

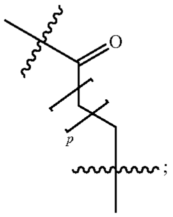

or

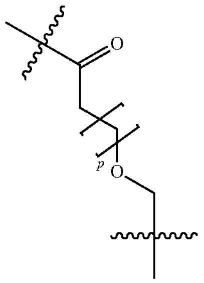

Wherein $R_2$ is selected from alkyl, aryl, alkoxy, aryloxy or arylalkyl groups;

"l", "m" and "p" each independently ranges from 0-15;

Comprising the steps of:

(i). Coupling a reactant selected from Glycolipid carboxylic acid of Formula (z-b)

Formula (z-b)

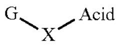

or a Glycolipid amine compound of Formula (z-bb) Formula (z-bb)

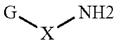

with esters of Formula (z-c)

Formula (z-c)

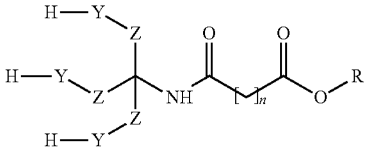

to form compound of Formula (Ia)

Formula (Ia)'

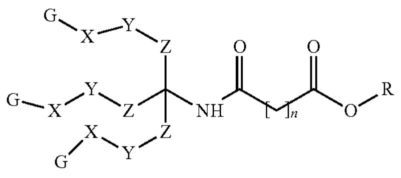

(ii). Subjecting the ester compound of Formula (Ia)' to hydrolysis in presence of enzyme selected from lipases, protease, amylase, trypsin, papain or combinations thereof, and water to obtain compounds of Formula (I)'.

7. The process according to claim 6, wherein the coupling at step (i) is in presence of a coupling agent selected from a group comprising hydroxybenzotriazole (HOBt), Hexafluorophosphate Benzotriazole Tetramethyl Uronium (HBTU), ethyl-(N',N'-dimethylaminojpropylcarbodiimide hydrochloride (EDC·HCl) or combinations thereof.

8. The process according to claim 6, wherein the coupling reaction at step (i) is conducted in the presence of a base selected from N,N-diisopropylethylarmne (DIPEA).

9. The process according to claim 6, further comprising:

Subjecting the Glycolipid carboxylic ester of Formula (z-a)

Formula (z-a)

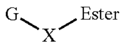

to hydrolysis in presence of enzyme and water to obtain Glycolipid carboxylic acid of Formula (z-b).

10. The process according to claim 6, wherein the compound of Formula (I)' is selected from:
1-e
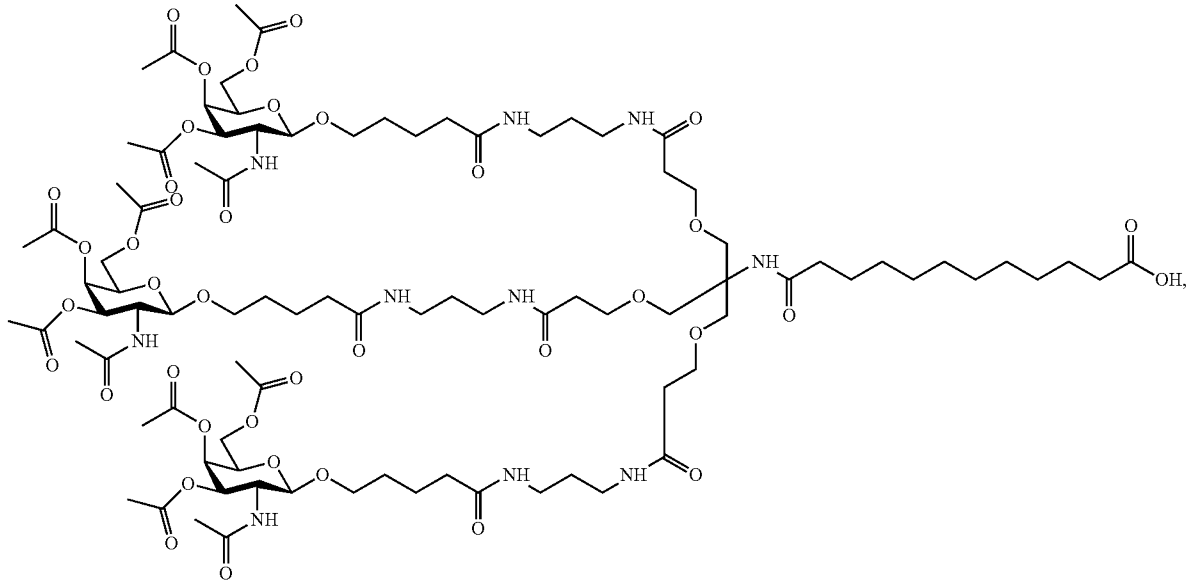
2-e
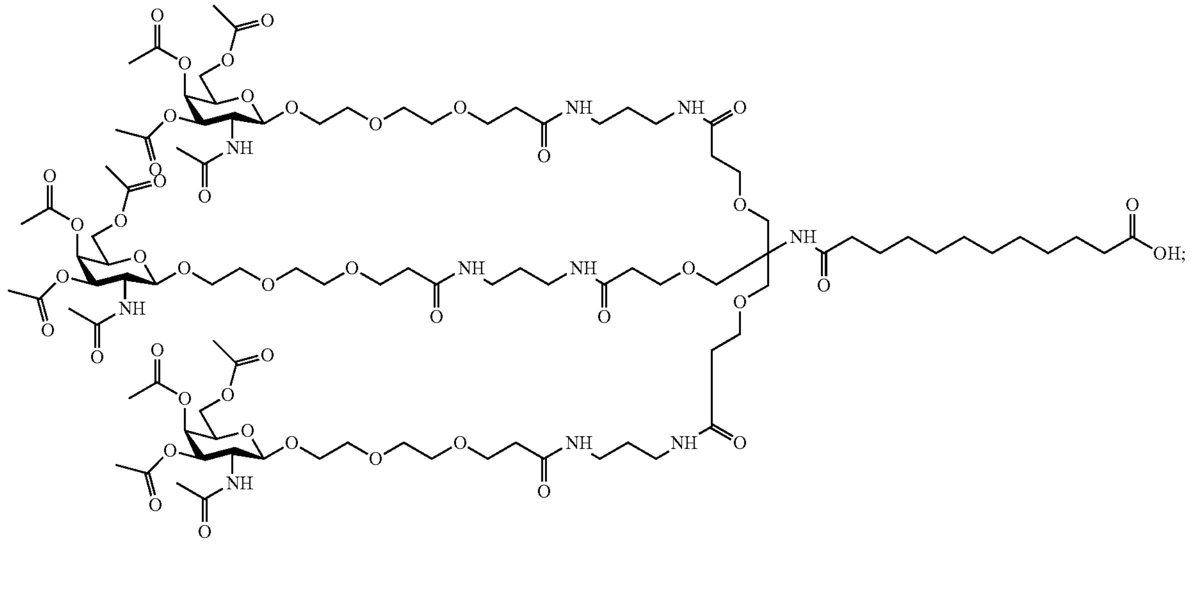

-continued
3-e
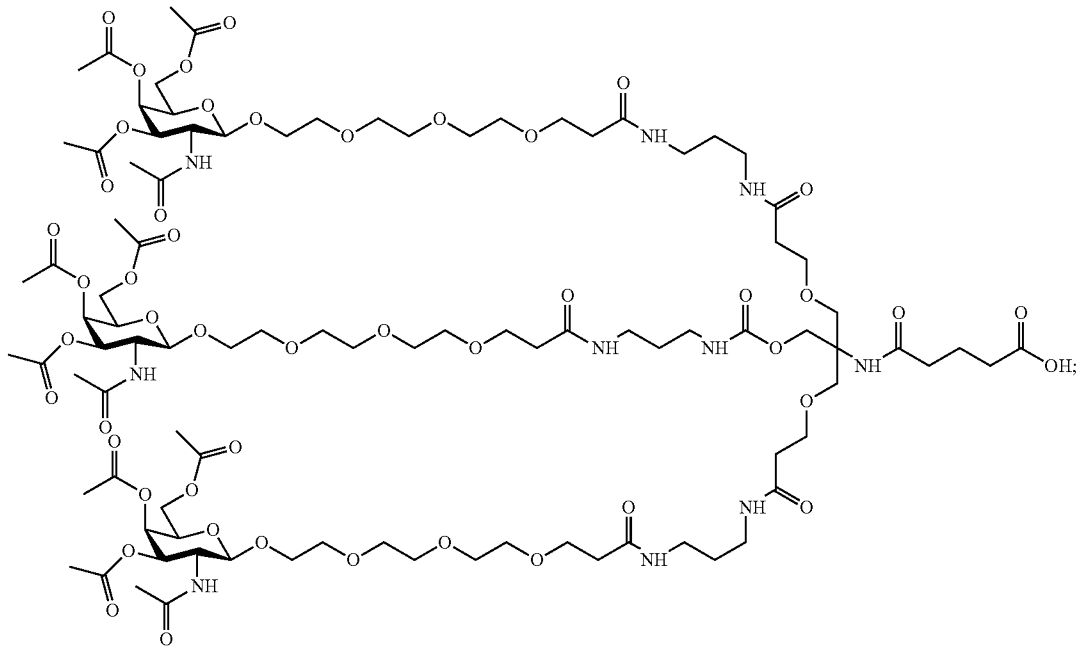
4-d
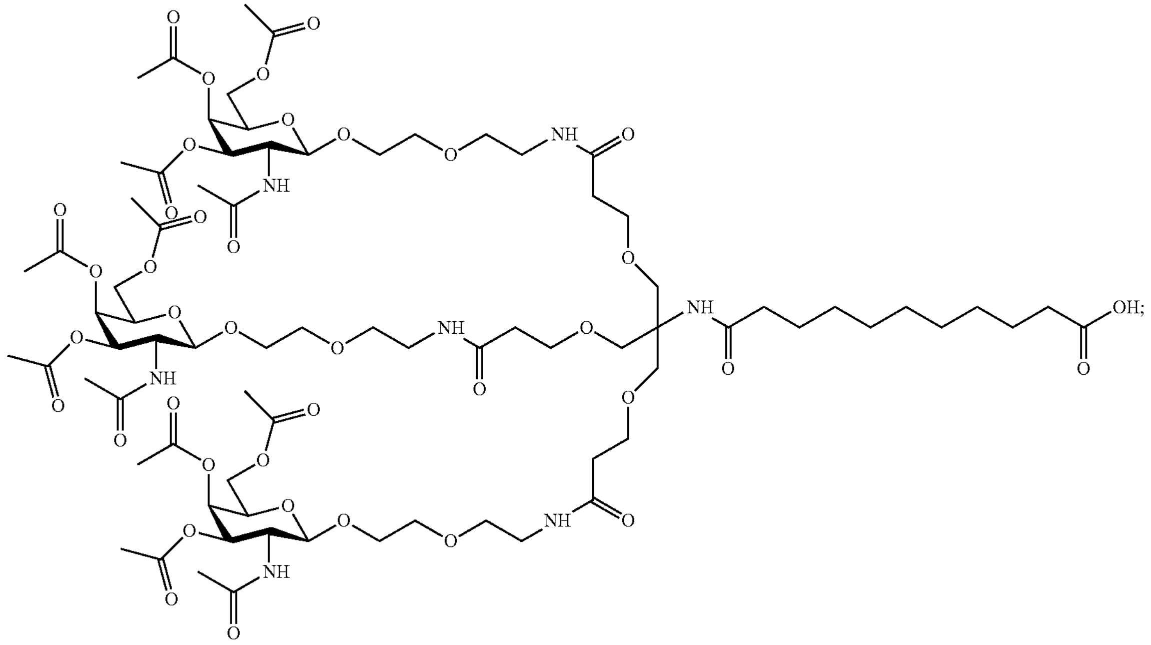

-continued
5-d
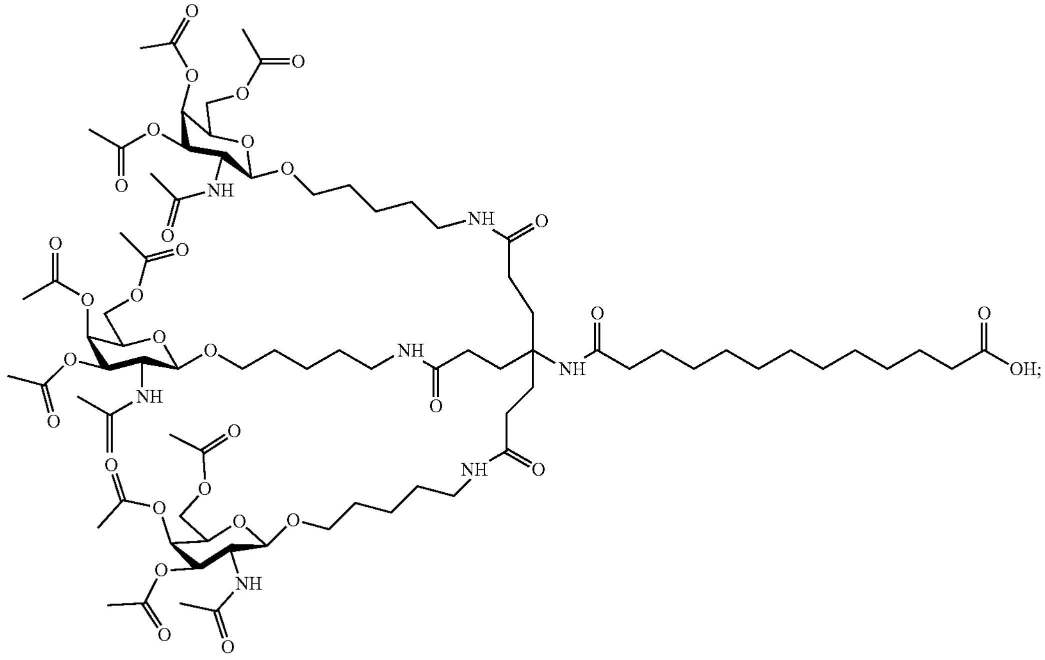
6-e
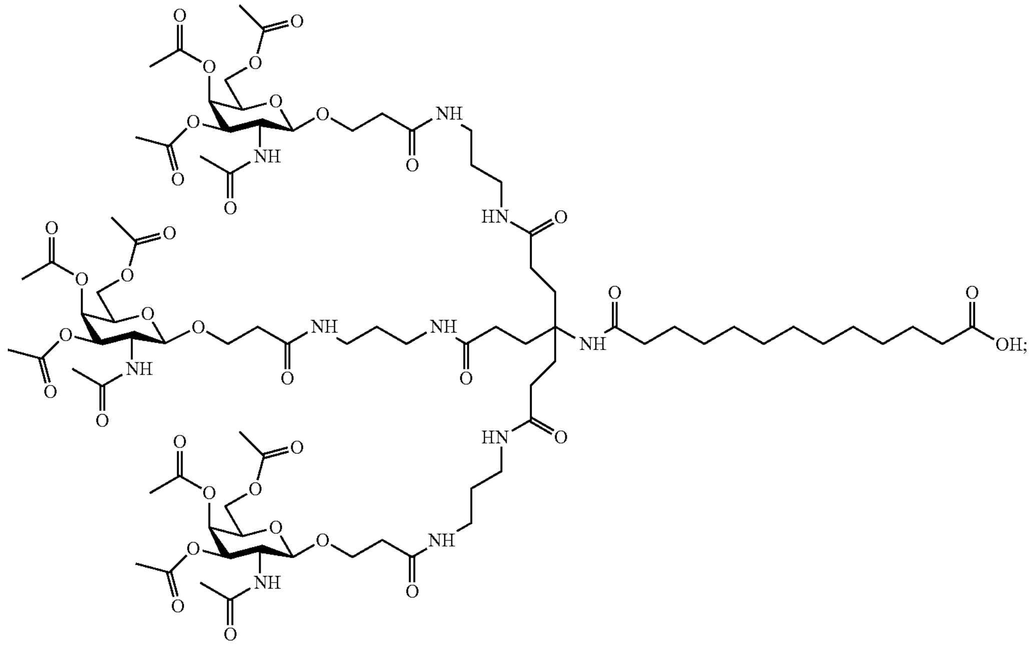
or

-continued
7-d
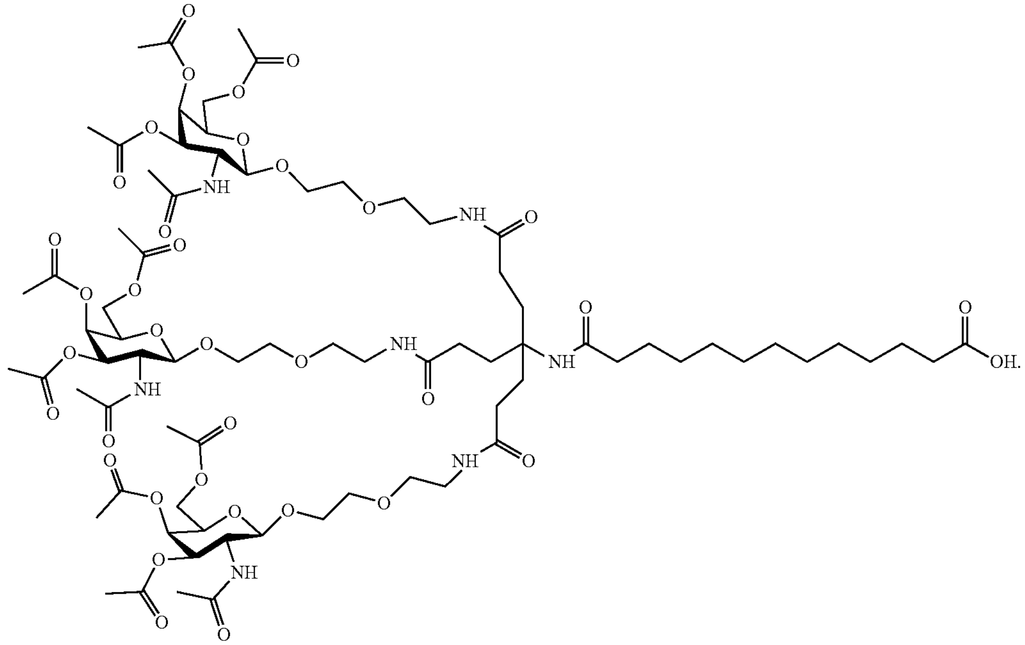
11. A process for preparing a compound of Formula (1-e)
1-e
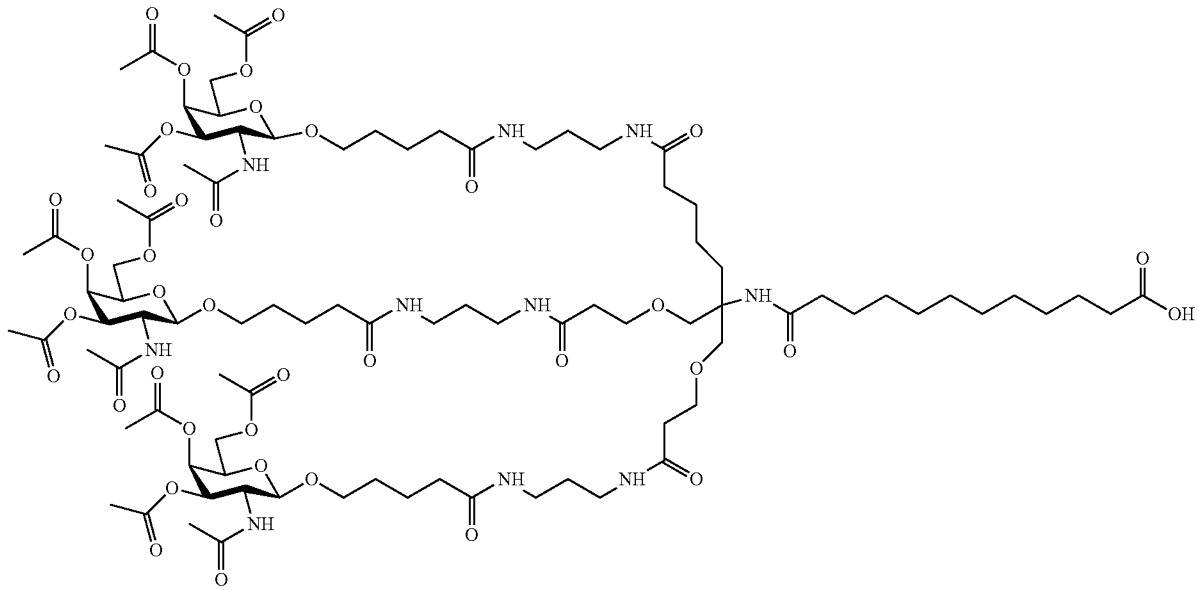

comprising the steps of:
(i). Subjecting the Glycolipid carboxylic ester of Formula (1-a) to hydrolysis in presence of enzyme and water;
1-a
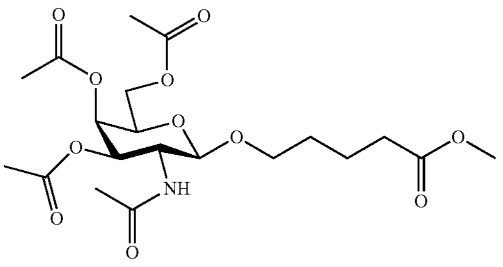
to form Glycolipid carboxylic acid of Formula (1-b)
1-b
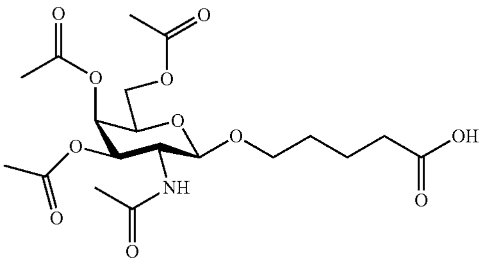
(ii). Coupling compound of Formula (1-b) with esters of Formula (1-c)
1-c
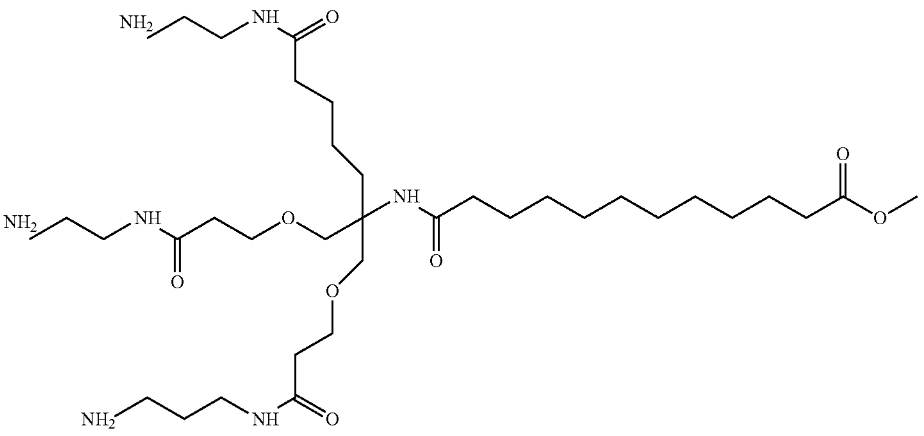

to form compound of Formula (1-d)
1-d
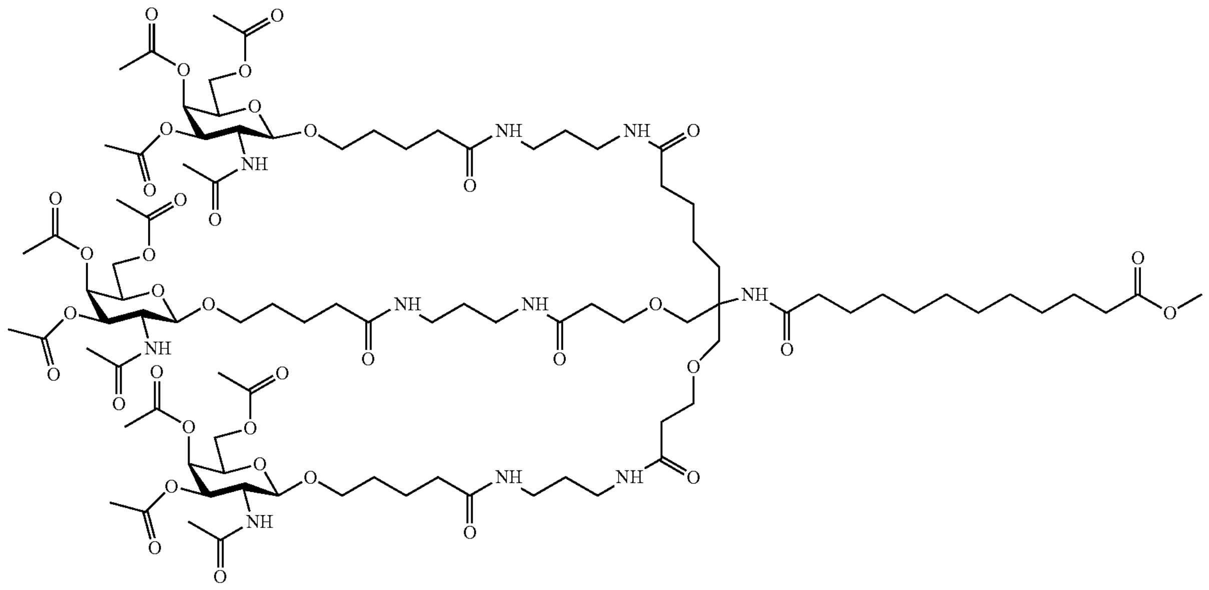

(iii). Subjecting the ester compound of Formula (1-d) to hydrolysis in presence of enzyme and water to obtain compounds of Formula (1-e).

* * * * *